(12) United States Patent
Gokcen et al.

(10) Patent No.: US 6,296,847 B1
(45) Date of Patent: *Oct. 2, 2001

(54) COMPOSITION FOR TREATING BENIGN PROSTATIC HYPERTROPHY

(75) Inventors: Muharrem Gokcen, Minneapolis; Terry J. Guy, Chaska, both of MN (US)

(73) Assignee: Immunolytics, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/154,158

(22) Filed: Nov. 17, 1993

Related U.S. Application Data

(63) Continuation of application No. 07/707,662, filed on May 30, 1991, now abandoned, which is a continuation of application No. 07/429,966, filed on Oct. 31, 1989, now abandoned, which is a continuation-in-part of application No. 07/303,809, filed on Jan. 27, 1989, now abandoned.

(51) Int. Cl.$^7$ .................................................. A61K 38/54
(52) U.S. Cl. ................... 424/94.2; 424/94.6; 424/94.61; 424/94.67; 514/968; 514/975
(58) Field of Search ................................. 424/94.2, 94.6, 424/94.61, 94.67; 514/968, 975

(56) References Cited

U.S. PATENT DOCUMENTS

| | | | |
|---|---|---|---|
| 3,678,158 | 7/1972 | Sussman | 424/94.67 |
| 3,691,090 | 9/1972 | Kitajima et al. | 252/316 |
| 3,792,161 | 2/1974 | Fox | 424/94.67 |
| 3,977,408 | 8/1976 | MacKew | 128/349 B |
| 4,005,194 | 1/1977 | Johnson | 514/2 |
| 4,174,389 | 11/1979 | Cope | 424/67 |
| 4,224,179 | 9/1980 | Schneider | 252/316 |
| 4,224,313 | 9/1980 | Zimmerman et al. | 424/94.3 |
| 4,276,281 | 6/1981 | Crikelair | 424/84 |
| 4,276,284 | 6/1981 | Brown | 424/530 |
| 4,310,523 | 1/1982 | Neumann | 424/240 |
| 4,317,817 | 3/1982 | Blohm | 424/226 |
| 4,317,818 | 3/1982 | Benson et al. | 424/242 |
| 4,329,430 * | 5/1982 | Klein | 435/219 |
| 4,338,300 | 7/1982 | Gelbard | 424/94.67 |
| 4,440,749 | 4/1984 | Fujisaki et al. | 424/94.63 |
| 4,446,129 | 5/1984 | Sawada | 424/94.6 |
| 4,485,095 | 11/1984 | Fujisaki et al. | 424/94.6 |
| 4,524,065 | 6/1985 | Pinnell | 424/94.2 |
| 4,568,543 * | 2/1986 | Borrelli | 424/94.63 |
| 4,645,668 * | 2/1987 | Pinnell | 424/94.2 |
| 4,659,695 * | 4/1987 | Labrie | 514/15 |
| 5,116,615 * | 5/1992 | Gokcen et al. | 424/94.2 |

OTHER PUBLICATIONS

Van de Graaff & Fox, Concepts of Human Anatomy & Physiology, W C Brown, 1986.*
Marieb, Human Anatomy & Physiology, 2d ed, Benjamin/Cummings, 1992.*

J.T. Grayhack et al. in *Benign Prostatic Hyperplasia*; J.T. Grayhack, J.D. Scherbenske, Eds.; DHEW Publication No. (NIH 76–113); Bethesda, MD, 1975, p. 125, disclose the results of surgical treatment of BPH.

T.C. Ingl et al., *J. Urol.*, 137, 1189 (1987), disclose the results of surgical treatment of BPH.

J.T. Grayhack et al., in *Adult and Pediatric Urology*, J.T. Grayhack, Y.J. Gillenwater, Eds.; Yearbook Medical Press: Chicago, IL, 1987; vol. 2; p. 1062, disclose general information about BPH including medical treatment (see p. 1089).

S. Boyarsky in *Benign Prostatic Hypertrophy*; F. Hinman, Ed.; Springer–Verlag: New York, NY, 1983; p. 425, discloses certain pharmacologic treatments of BPH.

A. Yerushalmi et al., *J. Urol.*, 133, 873 (1985) disclose localized deep microwave hyperthermia in the treatment of BPH.

M.G. McLoughlin et al. in *Benign Prostatic Hypertrophy*; F. Hinman, Ed.; Springer–Verlag: New York, NY, 1983; p. 130, disclose a study of the stromal–epithelial interaction in BPH.

W.W. Scott et al. in *Benign Prostatic Hyperplasia*; J.T. Grayhack, J.D. Wilson, M.J. Scherbenske, Eds.; DHEW Publication No. (NIH 76–1113); Bethesda, MD, 1975, p. 135, disclose methods used to shrink the modular hyperplasia mass by hormonal manipulations.

G. Williams in *Endocrinology of Prostate Tumors*; R. Ghanadian, Ed.; MTP Press: Boston, MA, 1983; p. 263, discloses the response of BPH to endocrine therapy and hormonal therapy.

P.C. Walsh in *Campbell's Urology*; P.C. Walsh, R.F. Gittes, Eds.; W.B. Saunders: Philadelphia, PA, 1986; vol. 2; p. 1248, disclosed general information about BPH including treatment methods (see p. 1261).

A. Sjoerdsma, *Clin. Pharmacol. Ther.*, 30, (1981) discloses the use of suicide enzyme inhibitors in the treatment of BPH.

N. Sonino, *N. Engl. J. Med.*, 317, 812 (1987) disclosed the use of ketoconazole as an inhibitor of steroid production.

(List continued on next page.)

*Primary Examiner*—Jean C. Witz
(74) *Attorney, Agent, or Firm*—Merchant & Gould P.C.

(57) ABSTRACT

The invention provides a composition and method for treating benign prostatic hypertrophy in mammals so as to cause the dissolution and regression of hypertrophied prostatic tissue and thereby provide relief from the obstructive symptoms associated with the disease. The present composition preferably comprises a sterile pyrogen-free solution of the hydrolytic enzymes collagenase and hyaluronidase, a nonionic surfactant, and an antibiotic; all provided, in a pharmaceutically acceptable, buffered, isotonic, aqueous carrier. The present method preferably comprises the direct intraprostatic injection of a safe and therapeutically effective dose of the composition via the transurethral route of administration.

31 Claims, No Drawings

OTHER PUBLICATIONS

C.A. Peters et al., *N. Engl. J. Med.*, 317, 599 (1987) disclose the use of nafarelin acetate, a luteinizing–hormone releasing hormone agonist in the treatment of BPH.

M. Caine, *Seminars in Urology*, 3, 311 (1985) discloses the use of a Á–adrenergic blocking agents in the treatment of BPH.

C.P. Schaffner in *Process of Clinical and Biological Research*; G.P. Murphy, Ed.; A.R. Liss: New York, NY, 1981; vol. 75A; p. 294, discussed hypocholesterolemic agents and the prostate gland.

A. Choudhury et al., *British Journal of Urology*, 52, 204 (1980) disclose the use of intraprostatic phenol injections in the treatment of BPH.

W.E. Stamm et al. in *Harrison's Principles of Internal Medicine*; G.R. Petersdorf, Ed.; McGraw Hill: New York, NY, 1983; p. 1649, disclose general information about urinary tract infections, including prostatitis.

D.S. Coffey in *Campbell's Urology*; P.C. Walsh, R.F. Gittes, Eds.; W.B. Saunders: Philadelphia, PA, 1986; vol. 1; p. 233, discloses the general biochemistry and physiology of the prostate and seminal vesicles.

M. Charton et al., *J. Urol.* 138, 87 (1987) disclose a study of antibiotic prophylaxis of urinary tract infections after transurethral resection of the prostate.

E.W. Ramsey et al., *Urology*, 21, 376 (1983) disclose antibiotic prophylaxis of urinary tract infections after transurethral resection of the prostate.

M. Bhargava et al., *Indian J. Exp. Biol.*, 15, 762 (1977) disclose histopathological changes due to injection therapy of an enlarged prostate.

S.C. Kabra et al. in *Indian J. Exp. Biol.*, 15, 768 (1977) disclose the fate of fluid injection during injected therapy of an enlarged prostate.

J. Jhanwar et al., *Indian J. Exp. Biol.*, 15, 772 (1977) disclose injection of a carbolic acid–acetic acid–glycerine mixture and its effect on an enlarged prostate.

C.H.J. Ford et al., *Cancer Chemother. Pharmacol.*, 17, 197 (1986) disclose a review of antibody–mediated targeting in the treatment and diagnosis of cancer.

L. Baert et al., *Urology*, 21, 370 (1983) disclose the treatment of chronic bacterial prostatitis by local injection of antibiotics into prostate.

E.M. Meares, Jr. in *Campbell's Urology*; P.C. Walsh, R.F. Gittes, Eds.; W.B. Saunders: Philadelphia, PA, 1986; vol. 1; p. 868, discloses general background information on prostatitis and related disorders.

M.I. Resnick in *Benign Prostatic Hyperplasia*; J.T. Grayhack, J.D. Wilson, M.J. Scherbenske, Eds.; PHEW Publication No. (NIH 76–1113); Bethesda, MD, 1975; p. 249, discusses various techniques of prostatic perfusion used in BPH experimental treatment.

I. Mandl in *Collagenase*; I. Mandl; Gordon & Breach: New York, NY, 1972; p. 1, discloses general information about, and various uses of, collagenase.

M.M. Webber, *In Vitro*, 15, 967 (1979) discloses the use of collagenase for tissue dissociation in the isolation of normal and benign human prostatic epithelium in vitro.

A.M. Boxer et al. in *Collagenase*; I. Mandl, Ed.; Gordon & Breach: New York, NY, 1972; p. 155, discloses the use of collagenase in the debridement of burns and ulcers.

M.M. Levi in *Collagenase*; I. Mandl, Ed.; Gordon & Breach: New York, NY, 1972; p. 197, disclosed the use of collagenase in gynecology.

F.W. Longo et al. in *Collagenase*; I. Mandl, Ed.; Gordon & Breach: New York, NY, 1972; p. 113, disclose the use of collagenase in the dissolution of "cyro–slough" following cryogenic surgery.

B.J. Sussman et al. in *Collagenase*; I. Mandl, Ed.; Gordon & Breach: New York, NY, 1972; p. 101, disclose the effect of collagenase on intervertebral discolysis.

T.E. Cawston et al. in *Methods in Enzymology*; L. Lorand, Ed.; Academic Press: New York, NY 1981; vol. 80; p. 711, disclose general information on mammalian collagenase.

E. Wunsch et al., *Z. Phisiol. Chem.*, 333, 149 (1963) disclose a new specific and rapid determination of collagenase.

*Pharmaceutical Enzymes Properties and Assay Methods*, R. Ruyssen et al., Ed.; E. Story–Scientia: Gent, Belgium, 1978; disclose general information about hyaluronidase and its therapeutic use.

P.R. Maroko et al., *N. Engl. J. Med.*, 296, 898 (1977) disclose the effects of hyaluronidase in reducing post–infarction myocardial necrosis.

A. Linker in *Methods of Enzymatic Analysis*; H.H. Bergmeyer, Ed.; Verlag Chemie: Deerfield Beach, FL, 1983; vol. 4; p. 256, discloses a method of analyzing hyaluronidase.

A. Abuchowski et al., *Biochim. Biophys. Acta*, 578, 41 (1978) disclose polyethylene glycol modified trypsin.

K.V. Savoca et al., *Biochim. Biophys. Acta*, 578, 47 (1979) disclose polyethylene glycol modified arginase.

G.L. Moore, *Anal. Biochem.*, 32, 122 (1969) discloses a method of measuring the activity of proteolytic enzymes.

*Biomedical Information*, J. Keesey, Ed.; Bolhringer Mannheim; Indianapolis, IN, 1987; 1st Ed.; p. 197, discloses information about Trition® X–100, a non–ionic polyoxyethylene detergent.

*Triton X–100 Material Safety Data Sheet*; Mallinckrodt Inc., Science Products Division; Paris, KY, 1985, discloses information about Triton X–100, specifically toxicity data.

H. Lepor, *J. Urol.*, 141, pp. 1283–1289 (1989).

J.T. Isaccs, *The Prostate Supplement 3*, Proceedings of the Urological Assoc. Meeting held May 6, 1989, pp. 1–3 (1990).

R.M. Levin et al., *The Prostate Supplement 3*, Proceedings of the Urological Assoc. Meeting held May 6, 1989, pp. 9–26 (1990).

R.C. Bruskewizt et al., *The Prostate Supplement 3*, Proceedings of the Urological Assoc. Meeting held May 6, 1989, pp. 27–38 (1990).

P.K. Reddy, *The Prostate Supplement 3*, Proceedings of the Urological Assoc. Meeting held May 6, 1989, pp. 39–48 (1990).

J.D. McConnell, *The Prostate Supplement 3*, Proceedings of the Urological Assoc. Meeting held May 6, 1989, pp. 49–59 (1990).

M.J. Barry, *The Prostate Supplement 3*, Proceedings of the Urological Assoc. Meeting held May 6, 1989, pp. 61–74 (1990).

H. Lepor, *The Prostate Supplement 3*, Proceedings of the Urological Assoc. Meeting held May 6, 1989, pp. 75–84 (1990).

P.G. Fabricius et al., *The Prostate Supplement 3*, Proceedings of the Urological Assoc. Meeting held May 6, 1989, pp. 85–93 (1990).

\* cited by examiner

COMPOSITION FOR TREATING BENIGN PROSTATIC HYPERTROPHY

This is a continuation, of application Ser. No. 07/707,662, filed May 30, 1991, now abandoned, which is a continuation of application Ser. No. 07/429,966, now abandoned, filed Oct. 31, 1989, which is a continuation-in-part of application Ser. No. 07/303,809, filed Jan. 27, 1989, (now abandoned).

FIELD OF THE INVENTION

The present invention is directed to a composition of hydrolytic enzymes for use in treating prostatic hypertrophy, particularly to the use of a composition comprising a mixture of collagenase, hyaluronidase, a nonionic surfactant, and an antibiotic, administered by intraprostatic injection to relieve the obstructive symptoms associated with benign prostatic hypertrophy in mammals.

BACKGROUND OF THE INVENTION

Benign prostatic hypertrophy (BPH) is one of the most common medical problems experienced by middle to older aged men. Urinary tract obstruction due to prostatic enlargement has been recognized since the earliest days of medicine. Hypertrophic enlargement of the prostate gland often leads to compression of the urethra resulting in obstruction of the urinary tract and the subsequent development of symptoms including frequent urination, nocturia, pain, discomfort, and embarrassment. The association of BPH with aging has been shown to exceed 50% in men over 50 years of age and increases in incidence to over 75% in men over 80 years of age. Symptoms of urinary obstruction occur most frequently between the ages of 65 to 70 when approximately 65% of the men in this age group have prostatic enlargement. Due to a continuing increase in life expectancy, the average age of the population of the United States is increasing. Accordingly, the number of men expected to develop clinical symptoms of BPH will also continue to increase.

Currently there is no effective nonsurgical method of treatment for BPH. Patients suffering from the obstructive symptoms of this disease are generally provided with only two options: continue to cope with the symptoms, or submit to surgical intervention. The incidence of BPH requiring surgical intervention has been found to increase progressively with age to a maximum of 11 per thousand in men more than 80 years of age. More than 350,000 patients per year undergo surgery for removal of prostatic tissue in the United States. It has been calculated that a 40 year old man has about a 10% chance of requiring a prostatectomy for benign disease if he lives to be 80 years old.

Those suffering from BPH are often elderly men, many with additional health problems that increase the risk of surgical procedures. Surgical procedures for the removal of prostatic tissue are associated with a number of hazards including: anesthesia associated morbidity; hemorrhage; pulmonary emboli; bladder perforation; incontinence; infection; urethral or bladder neck stricture; retention of prostatic chips; retrograde ejaculation; and impotence. Accordingly, a significant number of patients with symptoms severe enough to warrant surgical intervention are poor operative risks and are not able to undergo prostatectomy. There is no doubt regarding the need, importance, and value of an alternative nonsurgical method of treatment for those men who are poor surgical risks.

An alternative, nonsurgical method of therapy may be expected to yield savings in many areas such as: surgical costs; post-operative hospitalization; transfusion; antibiotics; out-patient visits; rehospitalization for complications; and other socio-economic costs related to recuperation and sick leave. The psychological complications of BPH in aging men due to loss of bladder control are significant. An alternative, nonsurgical form of therapy would improve the quality of life for many aging men in terms of frequency of urination, inconveniences, embarrassment, and loss of personal dignity. BPH is a disease with major costs for society. The development and implementation of an alternative nonsurgical therapy for BPH would provide major medical, economic, and psycho-social benefits.

Accordingly, a clear need exists for a safe, effective, nonsurgical treatment for prostatic hypertrophy. A further need exists for a treatment that poses little risk to the patient, is relatively inexpensive, and which can be performed as an out-patient procedure without the use of general anesthesia.

SUMMARY OF THE INVENTION

The present invention is directed to an enzyme composition and a method of using the enzyme composition for treatment of prostatic hypertrophy. The enzyme composition enzymatically dissolves prostatic tissue in order to relieve the obstructive symptoms of prostatic hypertrophy.

The method comprises administering by direct intraprostatic injection a therapeutically effective amount of a composition comprising an effective amount of hydrolytic enzymes, preferably two or more hydrolytic enzymes selected from the group consisting of collagenase, hyaluronidase, elastase, trypsin, chymotrypsin, pronase, DNase I, bromelain, clostripain, thermolysin, neuraminidase, phospholipase, cholesterol esterase, dispase, subtilisin, papain, chymopapain, plasminogen activator, plasmin, streptokinase, urokinase, fibrinolysin, serrathiopeptidase, pancreatin, amylase, lysozyme, cathepsin-G, and the PMN (polymorphonuclear) leukocyte serine proteases, provided in a pharmaceutically acceptable aqueous carrier. More preferably the hydrolytic enzymes comprise collagenase and at least one enzyme selected from the group consisting of hyaluronidase, trypsin, chymotrypsin, pronase, elastase, DNase I, dispase, and plasmin. Most preferably the hydrolytic enzymes comprise collagenase and hyaluronidase.

The present method preferably comprises the direct intraprostatic injection of a therapeutically effective unit dose of the composition, the composition preferably comprising collagenase and hyaluronidase in a pharmaceutically acceptable aqueous carrier, also preferably containing a surfactant and an antibiotic. The aqueous carrier is preferably sterile, pyrogen-free, buffered, and isotonic.

The compounds of the composition may be administered alone, sequentially, or preferably, combined with one another in the form of a liquid pharmaceutical unit dosage form suitable for injection. The dose of the composition administered may vary over a wide range as can readily be determined by the clinician. The preferred dosage for obtaining the desired therapeutic objective may vary depending on the age of the patient, nature and severity of disease, potency of the composition, and route of administration.

The preferred route of administration is by means of transurethral intraprostatic (intralesional) injection. Alternatively, the transperineal or transrectal routes of prostatic injection may be used. Treatment regimens encompassed by the present invention employ the intraprostatic injection of safe and effective amounts of the preferred composition in order to cause the solubilization and regression of obstructive prostatic tissue. The injections may be administered in daily, weekly, or monthly injection protocols until the therapeutically desired result is obtained.

The present invention is also directed to a kit comprising at least one separate injectable unit dosage of a pharmaceutical composition comprising an effective amount of the hydrolytic enzymes of the present invention, most preferably collagenase and hyaluronidase.

The terms "effective amount" or "effective concentration", as used to describe concentrations of components of the present invention, is defined as the amount of the component that, when in combination with the other components, provides the desired inhibition of growth, alteration of morphology, and reduction in size of the prostate for the given patient. The reduction in size of the obstructive prostatic tissue and the subsequent alleviation of symptoms of urinary obstruction are indicative of successful therapy. Objective assessment of the effects of the therapy is measured by standard methods including urodynamic flow analysis, transurethral examination, or transrectal ultrasonography in conjunction with an obstructive symptom scoring chart.

DETAILED DESCRIPTION OF THE INVENTION

BPH—Introduction to the Problem

The development of BPH is a phenomenon of aging men. The prostate weighs a few grams at birth and at puberty undergoes an androgen induced growth reaching the adult size of 20 g by the second decade of life. The prostate typically remains stable in weight and histological characteristics for about 25 years. In the fifth decade a second spurt of growth begins in most men. This second growth phase originates in the periurethral area of the gland as a localized proliferation of cells. Growth and enlargement may progress to compress the remaining normal gland, result in a major increase in gland size, and cause urinary and/or rectal obstruction.

BPH is believed to arise from an inner set of prostatic ducts and glands that reside within or adjacent to the urethral wall. The initial lesions are usually comprised of a tiny mass of loose connective tissue stroma lacking glandular components. However, as the nodule develops and grows, glandular tissue predominates. Once the hyperplastic process is initiated, all elements of the normal prostate (stromal, muscular, and glandular) participate to various degrees in the progressive growth. Determinations of the relative amounts of these tissues in patients with BPH have shown that the amount of fibromuscular tissue far exceeds the amount of glandular or epithelial tissue. The fibromuscular stroma composes approximately 45% of the volume of the normal prostate as opposed to approximately 60% in the hyperplastic gland.

Hypertrophy of the stromal and glandular (epithelial) components may occur alone or together. The variable response is evidenced by the nature of the nodules and their phases of development. The glands in the hyperplastic nodules seem to have the ability to bud and form new ducts and acini. Stromal nodules rarely reach large size, while clinically significant growths usually have large glandular components. Prostatic enlargement is often described in terms of enlargement of a glandular organ; however, smooth muscle is also an important component. The prostatic capsule possesses an even higher proportion of muscular tissue.

The primary symptom of benign enlargement of the prostate is urinary obstruction. Urethral obstruction occurs as a result of compression or elongation of the urethra. Benign nodular hyperplasia alone may cause urinary obstruction by physically obstructing the urethra or by interfering with the muscle or nerves supplying the urinary sphincter. The exact location of the nodular hyperplasia determines the speed and intensity of obstructive symptoms. A small strategically located nodule may cause more obstruction than larger more lateral hypertrophies that remain within the prostatic capsule. Hematuria is a common symptom of BPH because prostatic hypertrophy is a vascular growth with dilated veins on the urethral surface. Other irritative symptoms include increased frequency of urination and severe urgency that compels the passage of urine with a minimum of warning. The most serious complication of prostatic hypertrophy is the effect the obstruction has on the upper urinary tract. The obstruction may lead to hydronephrosis, severe renal damage, and potentially fatal uremia.

BPH Treatment Methods

Prior to the advent of surgical prostatectomy, the main form of therapy for BPH involved urinary diversion by catheter, either intermittently or continuously, with antiseptic irrigation of the catheter. The indications for an indwelling catheter included: male over age 50; diseased kidneys; atonic bladder; prostate of any size; catheterization possible without difficulty of complication; over four ounces of residual urine; feeble heart; vascular disease; and symptoms of urination frequency, pain, tenesmus, burning, epididymitis, and hematuria. Many patients with minimal symptoms from their obstruction were advised to tolerate their limited disability.

Prostatectomy is the currently accepted procedure for relieving bladder neck obstruction due to BPH. The goals of surgical treatment are to reverse and eliminate the effects of urinary obstruction such as renal failure, stone formation, and infection. Additionally, it is desirable to improve the quality of the patient's life by allowing him to void at normal intervals with good control and to allow normal sexual function. The indications for surgical prostatectomy include: male under 70 years of age; normal kidneys; fairly healthy bladder; marked enlargement of the prostate on rectal examination; decided urethral obstruction; over four ounces of residual urine; and symptoms of urination frequency, pain, tenesmus, burning, attacks of urethral fever, epididymitis, and hematuria. When patients have enough bladder neck obstruction to produce severe symptoms and are good surgical risks, removal of the obstructive prostatic tissue is usually advised by the suprapubic, retropubic, perineal, or transurethral route.

In the usual operations of prostatectomy, the hypertrophic nodules are shelled out leaving the compressed outer prostate, the so-called "surgical capsule" behind. Two of the common operative procedures employed for the removal of hyperplastic prostatic tissue involve a suprapubic incision. Suprapubic prostatectomy involves removal of the nodular hyperplasia through the bladder. Retropubic prostatectomy involves creating an incision on the ventral side of the prostatic capsule with subsequent removal of the offending nodules. An alternative procedure, the perineal prostatectomy is carried out using a perineal incision and removing the nodule through an incision in the dorsal side of the prostatic capsule. The most common surgical procedure used currently employs an endoscopic instrument passed through the urethra in order to remove hyperplastic or obstructive tissue in a piecemeal fashion (transurethral resection or TUR). Current techniques employing the return-flow resectoscope permit the continuous resection of prostatic tissue. A variety of other surgical approaches have been used sporadically with apparent relief of bladder neck obstruction due to BPH.

The rates of mortality for open surgical prostatectomy are essentially comparable for the various techniques, with the risk of mortality fluctuating around 1%. The risk of death is less in patients subjected to TUR. Patients with recognized renal failure are regarded as poor risks for prostatectomy. Men over 80 years of age are at greater risk as the mortality rate for TUR increases to 3.5%. Additionally, the risks of infection to which the patient is susceptible include standard operative wound infection, urinary tract infection, and bacteremia. Patients with very large adenomatous prostates are at the greatest risk for requiring transfusion whether the prostate is removed transurethrally or by open surgery. The various risks of blood transfusion including transmission of disease are well known.

Complications encountered by patients undergoing radical retropubic prostatectomy include: lengthy surgical time (range 1 to 6 hours); blood loss (range 50 to 7,000 ml); transfusions (range 0 to 20 units); rectal injury requiring colostomy, pelvic abscess, deep venous thrombosis, pulmonary embolism; and severe to total urinary incontinence. Minor complications include bladder neck contracture, temporary urine retention, urethral stricture, bladder or urethral rupture, epididymitis, prostatic/urethral strictures, urethral fistulas, and diminished sexual function.

Documented risks of TUR include incontinence, urethral stricture, bladder neck contraction, and sexual dysfunction. The patients who undergo this type of surgical removal of prostatic tissue face certain risks that include postoperative stress incontinence and absorption of irrigation fluid. Additional risks include bladder perforations, infections, and bleeding requiring transfusion. The average blood loss during transurethral resection of the prostate approaches 10 ml/g of tissue removed. Complications attendant with transurethral resection include: bladder spasms; hemorrhage; perforation of the bladder or prostatic capsule; damage to the urinary sphincter; and burn injury due to inadequate grounding of instrumentation. Post-operative complications associated with TUR include: hemorrhage; TUR syndrome; catheter malfunction; urethral strictures; bladder neck contractures; urinary tract infection; shock; deep vein thrombosis; pulmonary emboli; and disorders of the cardiovascular, gastrointestinal, and central nervous systems. Inappropriate healing at the bladder neck or scarring along the urethra can result in a narrowing of the urethral lumen due to formation of strictures or adhesions. Some strictures are easily controlled with little patient discomfort while others may require repeated surgical intervention.

Surgical procedures for removal of the prostate often require 1–3 hours for the operation followed by a week of hospitalization. Complications may extend the period of hospitalization to two or more weeks. Approximately 10–15% of the patients who undergo prostatectomy require further surgical intervention for the treatment of strictures with long term financial considerations. The incidence of recurrence of BPH following prostatectomy requiring repeat surgical removal varies from 0.3% with perineal prostatectomy to 7% after TUR. The higher incidence for TUR indicates a significant role for incompletely removed hyperplastic tissue in this procedure. Post surgical complications include total incontinence or such severe urgency or stress incontinence so as to require the use of a device in order to assure social acceptability. The need to use a device or prosthesis to achieve urinary control is an undesirable side effect of surgical prostatectomy. Patients who choose not to undergo surgical intervention must continue to live with pain and discomfort and most probably will develop more serious symptoms of prostatic obstruction in the future.

Current therapeutic attempts at relieving the clinical symptoms due to BPH focus upon removal of the obstructing tissue by surgery. Recently the combination of laser photocoagulation and vaporization techniques, along with hematoporphyrin photosensitization techniques, have been described as adjuncts to TUR surgical techniques. Problems associated with the use of laser therapy include difficulty in access to the prostate and variability in the depth of laser penetration. The prostate is only partially accessible with endoscopic instruments making the posterior lobe especially difficult to treat.

Localized deep microwave hyperthermia may be an alternative form of therapy to surgery in high risk patients with BPH. Microwave induced hyperthermia may be applied to the prostatic mass by means of a transrectal or transurethral applicator. Problems associated with this form of therapy are an inability to provide uniform and safe heating of the prostatic mass. Heating of normal tissue is unavoidable since high power field energies are required in order to gain access to the prostatic tissue.

BPH develops in man with aging and is believed to be the result of a changing cellular environment related to hormonal levels and interactions. Current information suggests that BPH is a hormone induced and controlled adenomatous growth. Recent understanding of the hormonal mechanisms underlying the pathogenesis of BPH has given impetus to endocrine related approaches for medical management of the disease. In these hormonal mechanisms, testosterone appears to be a prohormone, and dihydrotestosterone appears to be the active hormone for prostatic growth. It appears that the prostatic stroma contains an inductive mechanism that initiates the prostatic hyperplastic process, which is dependent upon a complex hormonal-stromal-epithelial interaction.

It is well known that castration effectively prevents BPH. The prostate, whether enlarged or normal, undergoes atrophy after orchiectomy and changes into a small tough fibrous mass in which there are only remnants of glandular tubules and ducts. Although this procedure was used at the turn of the century, it was abandoned in favor of excision of the obstructing tissue. Most attempts at controlling prostatic enlargement have centered on the administration of hormonal steroids and are based on the concept that castration results in symptomatic improvement and reduction in prostatic size by removal of the major source of androgenic stimulation. Specific antiandrogenic therapies have been directed at the inhibition of prostatic growth by preventing the onset of obstructive urinary symptoms or by inducing prostatic regression and involution, thereby relieving the symptoms of obstruction.

Efforts aimed at depriving the prostate of androgenic stimulation have taken a variety of approaches including estrogen therapy suppression of luteinizing hormone (LH) and antiandrogen therapy. Estrogen therapy for BPH is based on the fact that estrogens, in appropriate dosages, reduce the levels of circulating testosterone. Medical forms of therapy aimed at controlling BPH include the use of antiandrogens which inhibit prostatic growth yet do not produce deleterious side effects. Antiandrogens have been shown to competitively inhibit the binding of dihydrotestosterone to cellular receptors and to reduce testosterone concentrations in the male to castrate levels. However, once the antiandrogens are discontinued, the hyperplasia returns. Therefore, patients undergoing this type of therapy look forward to a lifetime of medication with the attendant undesirable side-effects of antiandrogenic therapy. Commonly reported side effects of this therapy include breast enlargement, nipple tenderness, loss of libido, impotence, and acne.

Testosterone is a prohormone that is converted to dihydrotestosterone in the prostate by the action of 5-α-reductase. As a result, the enzyme 5-α-reductase has been proposed as a target for the action of suicide inhibitors to reduce the levels of dihydrotestosterone. This has been shown to mediate benign prostatic enlargement. Steroid diazoketones have been shown to be unique analogs of the natural substrates for the enzyme 5-α-reductase and inhibit the enzyme's catalytic activity by forming covalent bonds in or near the enzyme's active site through diazonium alkylation.

Ketoconazole is an imidazole derivative that has been shown to be a potent inhibitor of gonadal and adrenal testosterone production. Ketoconazole does not appear to affect the pituitary in its secretion of LH; however, it does inhibit cholesterol synthesis, result in clinical reductions of adrenal and gonadal androgen levels, and is of low toxicity. The hormonal changes produced by the administration of ketoconazole are dose-dependent and fully reversible. The drug has been shown to be useful in clinical conditions that may benefit from inhibition of gonadal or adrenal steroid production. Ketoconazole has been shown to be a potent inhibitor of testosterone synthesis and may be of therapeutic benefit in the management of BPH. Potential side effects of ketoconazole therapy include decreased libido, impotence, gynecomastia, and hypogonadism.

Ornithine decarboxylase is an enzyme that is involved in the biosynthesis of the polyamines putrescine, spermidine, and spermine. These polyamines are thought to be involved in enhanced cellular growth and replication. Elevated levels of these polyamines are found in the prostate and other glands that are undergoing rapid proliferation. Upon the synthesis of potent suicide inhibitors of ornithine decarboxylase, such as DL-α-difluoromethyl-ornithine (DFMO), the prostatic levels of ornithine decarboxylase have been shown to be markedly reduced with the subsequent depletion of putrescine and spermidine. In animals, administration of the suicide inhibitor of ornithine decarboxylase, DFMO, has resulted in the inhibition of the growth of the prostate. Additionally, in tissue culture, DFMO inhibits DNA synthesis and slows the proliferation of human prostate adenoma cells. This compound may find application in the treatment of prostatic adenoma.

Additional attempts at the medical management of BPH as an alternative mode of therapy to surgical techniques have included the use of potent LHRH (luteinizing hormone releasing hormone) agonists which block testicular production of testosterone by inhibiting pituitary release of gonadotropins. The primary effect of LHRH agonists in humans is the reduction of serum testosterone levels. Leuprolide and nafarelin acetate have been shown to reduce circulating levels of androgens and estrogens in males to castrate levels within three weeks. These compounds in continuous and therapeutic doses desensitize the pituitary and block the release of sex steroid hormones. The degree of testosterone suppression achieved with potent LHRH agonists has been shown to be effective in the treatment of obstructive benign prostatic hypertrophy. Drawbacks to this form of therapy include the need to maintain medication indefinitely as androgenic suppression is reversible with subsequent regrowth of hyperplastic tissue. Furthermore, side effects include impotence, decreased libido, hot flashes, and may include an initial increase in obstructive symptoms.

Other efforts to prevent or treat BPH by nonsurgical means include the use of neuro-pharmacological agents such as α-1-adrenergic blocking agents. Prazosin, Hytrin, phentolamine, and ketanserin are anti-adrenergic drugs aimed at relaxation of the urinary sphincter mechanism. The pharmacologic treatment of BPH with α-adrenergic blockers provides a means for helping a large number of patients with prostatic enlargement in whom surgical intervention is not deemed necessary or has to be postponed. Various α-adrenergic blocking agents have been employed in the treatment of BPH and include the compounds phenoxybenzamine (potential mutagen), prazosin (Minipres), phentolamine (Regitine), nicergoline (Sermion), terazosin (Hytrin), and thymoxamine. Side effects are present in approximately 30% of the patients treated with phenoxybenzamine for BPH and include hypotension, dizziness, faintness, tachycardia, weakness, and retrograde or absent ejaculation. In about 10% of all cases treated, the side effects cannot be tolerated and therapy has to be abandoned. Prazosin and Hytrin seem to produce fewer side effects. The possibility of cerebral hypotension or ischemia appears to be a contraindication for these agents. Rapidly acting intravenous blockers such as phentolamine must be used with caution particularly in older age groups. However, nicergoline is thought to have a beneficial effect upon the cerebral circulation.

Pharmacologic evidence has shown that prostatic size in animals can be reduced subsequent to the lowering of serum cholesterol. Polyene macrolides have been shown to be effective and potent hypocholesterolemic agents. The polyene macrolides as a group have a specific physico-chemical affinity for sterols and sterol containing cellular membranes. The high cholesterol content of the prostate may be used as a target for pharmacological attack by lipid soluble or dispersing reagents such as the polyene macrolides. BPH is associated with an increase of cholesterol content and the deposition of cholesterol plaques in the lumen of the glandular alveoli and may account for the relatively high concentrations of polyene macrolides (lipid soluble) found in prostatic tissues. Based upon toxicity studies in animals, polyene macrolides have been shown to reduce serum testosterone levels, inhibit testicular function, and induce alterations in prostatic histology. The polyene macrolide antibiotics such as candicidin and amphotericin B have been shown to produce significant reductions in the volume of the prostate gland; however, human clinical trials have not shown a reduction in the number of patients requiring surgical intervention for obstructive symptoms due to BPH. Probucol and nystatin lower the cholesterol levels in the blood, but have failed to produce shrinkage of the prostate.

Various attempts at the nonsurgical treatment of the obstructive symptoms of BPH have been made, including phenol injection. Phenol injection therapy is based on the concept of chemical necrosis of prostatic tissue and subsequent shrinkage of the obstructive tissue. The therapy involves the intraprostatic injection of a solution of 2% liquid phenol, 2% glacial acetic acid, and 4% glycerin. The injection is accomplished by means of a lumbar puncture needle inserted perineally and guided into the prostate by means of digital rectal palpation. Reports of successful results are countered by complications including hemorrhage, impotence, exacerbation of symptoms, and injection pain or discomfort lasting from a few hours to several days. Injection therapy employing phenol appears to be an inadequate form of treatment for BPH as it fails to have a significant effect on the size of the prostate or upon urinary flow.

In summary, surgery is the only known realistic and effective treatment for the relief of urinary obstruction. Over the past 40 years, many attempts have been made at the medical management of this disease. The interpretation of the results of these attempts has been complicated by the fact that patients with symptoms attributable to BPH often experience temporary improvement or remission of voiding symptoms following diagnostic instrumentation alone. It is apparent that the various alternative nonsurgical therapies using estrogens, anti-androgens, and adrenergic blocking agents have had limited clinical success because compelling evidence of their efficacy does not exist. The effects of these therapies vary with the method of evaluation, mode and duration of therapy, and type of BPH encountered. None of the forms of medical management currently available is likely to be utilized as a long-term therapeutic alternative to surgery in patients with BPH.

The present invention provides an alternative, nonsurgical, nonradical procedure for treating and alleviating the symptoms of lower urinary tract obstruction due to BPH in mammals. The practice of the invention results in the inhibition of growth, alteration of morphology, and the reduction in size of an undesirably large prostate. The present invention decreases morbidity and improves the quality of life over currently employed surgical techniques designed to accomplish the same goals. Direct injection of the prostate is generally a safe, simple, and effective means of introducing the compositions of the present invention directly into the body of the enlarged prostate. The composition of the invention is safe and effectively causes the dissolution, regression, and involution of the stromal, epithelial, and fibromuscular components of prostatic tissue.

Human Prostate—Anatomy and Histology

The human prostate is a compact musculo-glandular organ that lies at the base of the bladder surrounding the urethra. The adult gland is about the size of a chestnut, weighs approximately 20 g and resembles a blunted cone. The prostate measures about 4.5 cm across its base with a length of 3.5 cm, narrowing to 2.5 cm across the anterior portion of the cone. The urethra runs through the approximate center of the prostate from base to apex and provides a key anatomic reference point for describing the various regions of the prostate.

The human prostate is firm in consistency and is surrounded by a prominent, fibroelastic structure of connective tissue and smooth muscle fibers, known as the capsule. Periodically, distinct septa emanate from the capsular sheath and penetrate the interior of the gland separating it into lobules. The periphery of the capsule is composed primarily of fibroblasts, collagen, and elastic fibers. The septa are abundant in smooth muscle cells.

The prostate is composed of a large number of glands that open by separate ducts into the urethra and are embedded in a stroma that is a mixture of collagenous and smooth muscle fibrous connective tissue. The prostate gland is imperfectly divided into 3 to 5 lobes by the ejaculatory ducts which pass through the prostate. Each lobe is further imperfectly subdivided into lobules. The prostate is composed of 30 to 50 lobules which open directly into the prostatic urethra through 15 to 30 ducts. The area of the gland between the urethra and the ejaculatory ducts is composed of small mucosal and medium sized submucosal glands while the rest of the prostate contains larger and more highly branched glands.

The human prostate is a tubuloalveolar gland with epithelium, smooth muscle, elastic tissue, and collagenous stroma arranged in a pattern that allows secretion to be stored and released when required into the urethra through the prostatic ducts. The human prostate is composed of alveoli and tubules both of which are lined with tall columnar or cuboidal epithelial cells. The glandular epithelium is highly variable ranging from simple columnar or pseudostratified to cuboidal. The epithelial cells rest on a layer of connective tissue rich in capillaries, collagen, and elastic fibers. The glandular excretory ducts are lined by simple or pseudo-stratified columnar epithelium merging with transitional epithelium as the ducts enter the urethra. There is a thick network of elastic fibers around the larger ducts and urethra.

The alveoli and ducts are embedded within a stroma of fibromuscular connective tissue. The stroma is made up of collagen and elastic tissue with many smooth muscle fibers arranged around the ducts and acini and between the glandular lobules. The highly vascularized stroma forms fairly well defined septa that radiate from, and form a thick ring of muscular tissue around, the urethra, known as the urethral sphincter. At the periphery of the gland, the stroma is condensed to form a capsule of circular strands of collagen, elastic tissue, and smooth muscle.

Blood vessels, lymphatics, nerves, and ganglia are found in the capsule and stroma. The inferior vesical artery, a branch of the anterior hypogastric artery, provides the major arterial blood supply to the prostate. The anterior division of the internal iliac artery supplies the prostate with accessory vessels, generally via branches of the middle hemorrhoidal and internal pudendal arteries. The prostate is innervated by the pelvic (autonomic) plexus and receives contributions from both the sympathetic and parasympathetic divisions of the autonomic nervous system.

The human prostate is anatomically heterogeneous and is composed of four morphologically distinct regions, only one of which is believed susceptible to BPH. These regions are not identifiable on external inspection and they are not easily or reliably separated by gross dissection. Four zones within the prostate have been identified with morphologic, functional, and pathologic importance: the anterior fibromuscular stroma; the peripheral zone; the central zone; and the periurethral zone.

BPH arises almost exclusively from a small portion of the prostate which immediately surrounds the prostatic urethra and the pre-prostatic sphincter. BPH is a nodular, regional growth due to an irregular mixture of glandular and stromal tissue. The hyperplastic tissue is usually located centrally in the periurethral portion of the enlarged gland. This anatomic location is responsible for the urinary obstructive symptoms associated with BPH and explains the severe symptoms often seen with only modest degrees of prostatic enlargement. The gross anatomy of most human prostatic hyperplasias appears as a whorled nodular growth with a relatively clear separation of normal from abnormal tissue. Upon microscopic examination, all of the glandular and stromal elements of the normal prostate are involved to various degrees in the hyperplasia.

It is thought that the pathogenesis of BPH may be due to the proximity of the glandular tissue to the stroma of the sphincter. Embryonic-like inductive interactions between these two tissue types may be involved in nodule generation. The earliest stage of BPH nodule formation has been described as a tiny mass of loose, embryonic-appearing stroma, completely lacking in glandular components. Later, glands adjacent to the mesenchymal nodule form branches that penetrate into the stromal mass and add epithelial components. Nodules of this type are most frequently found in the periurethral zone. However, in the central zone, the majority of small nodules appear to be predominantly glandular at inception. Additionally, the glands lie within a normal-appearing stroma that is not increased in amount and does not possess mesenchymal characteristics.

The growth of BPH has a neoplastic character with lesions appearing in the form of nodules that have multiple sites of origin within the periurethral region and grow without limits. The nodules are composed of varying proportions of three distinct tissue types and are not a diffuse hyperplasia or hypertrophy of pre-existing prostatic glands. The early. lesions are fibromyomas, which probably originate as a proliferation of smooth muscle and connective tissue that surround the periurethral glands and ducts. These early nodules may vary in composition from pure fibromuscular tissue with little or no epithelial components to adenomas in which the epithelial components are profuse with the original surrounding fibromuscular stroma rather prominent.

The human prostate undergoes two clinically important changes with age, benign prostatic hypertrophy and invasive carcinoma. Human BPH consists of the growth of multiple fibroadenomatous nodules that compress the surrounding normal prostatic tissue. The nodules arise in the inner region of the prostate, surround and distort the urethra, and compress the outer portion of the gland so that it forms the false or surgical capsule. Benign prostatic enlargement seems to arise in an inner (periurethral) gland group. While hyperplasia is developing in the inner group of glands, the outer group of glands begin to atrophy. Prostatic cancers tend to develop in the outer atrophic glands and rarely arise from benign hyperplastic glands. In cases where tumors appear to be present in the inner glands, multiple sections usually show that these growths are extensions from larger tumors in the outer glands. Carcinoma of the prostate is intimately associated with senile atrophy and probably arises from epithelial cells which have previously undergone atrophy. The compressed atrophic glands outside of the expanding nodules of hypertrophy are the most common sites of origin of prostatic carcinoma.

Frequently, the prostate glands of elderly men are affected by both BPH and carcinoma. Depending on age, 2% to 60% of the patients undergoing TUR for benign prostatic enlargement are found, upon histologic examination of the resected tissue, to have unsuspected prostatic carcinoma; since, many nonmetastasizing prostatic cancers are relatively asymptomatic.

Human Prostate Biochemistry

The prostate is a secretory gland whose complex and unique products are involved in the process of insemination. The secretions also provide protection against urinary tract bacterial infections. The secretions of the prostate are a product of the glandular epithelium with the secretory process described as both apocrine and merocrine.

With aging, the human prostate grows in size, changes structure and secretory activity, but does not appear to be deprived of hormonal support in spite of reduced levels of circulating androgens. Both testicular and adrenal androgens appear to support prostatic growth. Pituitary hormones and cyclic AMP may play a role in the development of the structural or functional changes that accompany the malignant transformation of prostatic tissues.

Benign enlargement of the prostate is a disease of advancing age. The initial lesions of BPH arise in the stromal component of the prostate and predominate over the epithelial components. The fibromuscular stroma of the prostate is rich in collagen and proteoglycans. Prostatic size may be regulated by a feedback system resulting in a balance between collagen production and collagen breakdown due to collagenolytic enzymes secreted by the epithelial cells. It is believed that the synthesis of prostatic collagen is dependent upon androgenic stimulation with the fibroblasts of the stroma stimulated by androgen to produce new collagen. These newly produced collagen fibers provide the network for new, anchorage dependent epithelial growth and proliferation. The increase in collagen is countered by a breakdown of collagen due to the action of an intraprostatic collagenolytic enzyme secreted by the epithelial cells. When the amount of androgen stimulated stromal growth exceeds the collagenase mediated breakdown of collagen, prostatic hypertrophy develops resulting in an increase in prostatic size.

Collagen is the major fibrous component of prostatic extracellular connective tissue. Collagen fibers provide a chemically and physically stable network or matrix of supporting connective tissue for the prostate and serve a variety of functions. Collagen functions biologically as a structural and supporting component of the extracellular matrix and as a substrate for cell adhesion. Collagen influences cellular proliferation and differentiation. Collagen also forms an integral part in the architecture of cellular basement membranes and cytoskeleton. The triple helical structure of the molecule endows collagen with a high resistance to proteolytic degradation.

Collagen is composed of fibrils of aggregated tropocollagen molecules. Each tropocollagen molecule includes three chains wrapped in a triple-helix. Tropocollagen molecules combine in aggregates forming cross-links, which continue to develop over time resulting in the collagen becoming more insoluble and resistant to lysis with aging. An increase in the hydroxyproline content of collagen provides a mechanism for the progressive rigidity of the structure of collagen with aging.

The connective tissue of the prostate is primarily comprised of collagen types I and III whose fibers constitute the bulk of the intercellular collagen. Collagen types IV and V are found mainly in the basement membrane of cells. The different types of collagen exhibit different susceptibilities to proteinases which are apparently due to variations in the tropocollagen primary amino acid sequence, the nature of covalently bound carbohydrates, and in the nature and degree of intermolecular cross-links. The resistance of collagen to proteolysis is thought to be due to its tightly coiled triple-helical structure. The helix is wound such that peptide bonds linking adjacent amino acids are buried deep within the interior of the molecule. As a result, the triple-helical region is highly resistant to attack by strong general proteases such as pepsin.

The initial proteolytic action of collagenase on collagen appears to be the hydrolysis of the triple-helical portion of the molecule splitting all three chains. A second cleavage of these chains then occurs producing many smaller fragments. The more highly cross-linked the collagen, the more resistant collagen becomes to the action of collagenase. Enzymatic breakdown of highly cross-linked collagen may require the cooperation of several enzymes: those that denature the triple helical structure; those that digest the polypeptide chains of denatured collagen; and those that split the end region of the collagen molecule, which is the site of intermolecular cross-linking.

Proteolytic solubilization of collagen may be inhibited by large amounts of collagen associated proteoglycans. The type of collagen, age of the tissue, degree of hydration, and the nature of associated proteoglycans are all factors that determine the nature of proteolytic degradation of collagen by the various proteinases. Proteolytic removal of the non-collagenous matrix surrounding the collagen fibers may be necessary before the actual digestion of collagen can take place. The collagen fibers of prostatic nodules are embedded in proteoglycans that inhibit collagenase from breaking down collagen. The use of hyaluronidase in the composition of the present invention has been found to overcome this inhibition.

The connective tissue stroma or extracellular matrix of the human prostate is composed of collagens, elastins, and the basement membrane proteins, fibronectin and laminin. The ground substance in which these components are embedded is composed of proteoglycans, complex polysaccharides, and glycolipids. The extracellular matrix of the prostate is intimately involved in the control of cell growth, differentiation, migration, and shape. The matrix is a stable material that lies under the epithelial cells, surrounds connective tissue cells, and provides the supporting network upon which cells reside. Collagens provide strength to the tissues, elastins provide resiliency, and proteoglycans provide the cohesive factors of the tissue matrix.

Proteoglycans contain a core protein bound covalently to at least one chain of glycosaminoglycan (GAG). Proteoglycans exhibit a wide range of core proteins with different classes, numbers, and lengths of glycosaminoglycans. Most of the mass of the proteoglycan consists of GAG chains composed of chondroitin sulfate, keratin sulfate, and heparin sulfate. The core protein and GAG chains interact with, and bind strands of, hyaluronic acid. The association between these three molecules results in a stable structure, composed of hyaluronic acid interposed between adjacent proteoglycans, that is accessible to the enzyme hyaluronidase.

Connective tissue stromal cells of the prostate include smooth muscle cells, fibroblasts, and primitive mesenchymal or endothelial cells. Cell-collagen binding is mediated by specific glycoproteins that are important in the adhesion, growth, differentiation, and transformation of cells. The prostatic extracellular matrix contains a number of high molecular weight glycoproteins including fibronectin, and laminin. Fibronectin is produced mainly by fibroblasts, mesenchymal cells, and smooth muscle cells, and adheres strongly to collagen, heparin, and DNA. Fibronectin appears to enhance the binding of smooth muscle cells to collagen types I and III. Smooth muscle cells preferentially attach to Type V collagen, and apparently attach directly to Type V collagen without requiring additional adhesive glycoproteins. Laminin is synthesized by epithelial cells, which attach preferentially to collagen Type IV. Laminin is the glycoprotein of the basement membrane that mediates the attachment of these cells to collagen. This basement membrane is a complex structure containing collagen Type IV, glycosaminoglycans, complex polysaccharides, and glycolipids. The basement membrane of the cell forms the interface with the stroma.

There are a large number of collagens, glycoproteins, and proteoglycans that form connective tissue. The interaction of proteoglycans and collagen results in the formation of the intercellular matrix of prostatic connective tissue. Within the stroma and connective tissue of the prostatic extracellular matrix is an intricate network of glycosaminoglycans and complex polysaccharides which include dermatan sulfate (40%), glycosaminoglycan, heparin (20%), chondroitin (16%), and hyaluronic acid (20%). A progressive loss of soluble hyaluronic acid and the conversion of chondroitin-4-sulfate to chondroitin-6-sulfate occurs with age.

Enzymes of the Present Composition

The present invention provides a composition which comprises a mixture of hydrolytic enzymes that can be used to digest or dissolve prostatic tissue and relieve the obstructive symptoms of prostatic hypertrophy. It has been found that a preferred embodiment comprises an effective amount of collagenase in combination with at least one enzyme selected from the group consisting of hyaluronidase, trypsin, chymotrypsin, pronase, elastase, DNase I, dispase, and plasmin. The use of collagenase in combination with hyaluronidase is particularly preferred.

A. Collagenase

Bacterial collagenase (such as *Clostridium hystolyticum*, EC 3.4.24.3) is thought to degrade collagen into small peptides by hydrolysis at several sites along the triple helix. Collagenase derived from *Clostridium hystolyticum* is commercially available, and purified preparations are available which are free from bacteria, spores, fungi, yeasts, mycoplasmas, and viruses. Bacterial collagenase is an extracellular enzyme secreted when *Clostridium hystolyticum* is cultured under appropriate conditions and is preferred.

Collagenase is a metalloenzyme that contains $Zn^{2+}$ in its active site. The collagenase derived from *Clostridium hystolyticum* has a molecular weight of about 105,000. Collagenase has no free sulfhydryl (SH) groups or disulfide bonds. Collagenase exhibits an isoelectric point of 8.6. $Ca^{2+}$ ions are required for binding the enzyme to the collagen substrate and to provide the enzyme with the required conformation for full catalytic activity. All other metals other than $Ca^{2+}$ inhibit collagenase; however, $Zn^{2+}$ is essential in limited concentrations.

Collagenase is irreversibly inhibited by cysteine and reversibly inhibited by EDTA, which binds essential $Ca^{2+}$. Cysteine appears to act as a chelating agent for zinc, which is the metallic ion located in the active center of the enzyme. Histidine has been shown to inhibit collagenase activity. Collagenases have also been shown to be inhibited by various metal-chelating agents such as o-phenanthroline and 8-hydroxyquinoline. Specific antisera do not appear to inhibit collagenase, and there is little or no inhibition of collagenase activity by normal serum. In general, bacterial collagenases are not inhibited by the naturally occurring inhibitors of tissue specific collagenases such as α-1-antitrypsin and α-2-macroglobulin. The optimal pH for collagenase activity is in the range of 6 to 8. Low pH values irreversibly inactivate the enzyme, and acetic acid may be used to stop the action of collagenase immediately. Furthermore, cortisone preparations have been found to enhance collagenase activity, and most antibiotics tested have been shown to be compatible with collagenase.

Collagenase digests triple-helical collagen fibers found in connective tissue typically resulting in fragments weighing about 600 to 700 daltons. Collagenase exhibits a specificity for the amino acid sequence -Pro-X-Gly-Pro-Y with cleavage occurring between X and Gly. Hydroxyproline may replace Pro, X is most often neutral, and Y is nonspecific. The enzyme's specificity is due to the repetitive occurrence of such sequences in collagen and the virtual absence of these sequences in other proteins.

In addition to the high degree of specificity collagenase exhibits for collagen, the enzyme is extremely stable in the presence of $Ca^{2+}$ ion and may be stored lyophilized and desiccated at 4° C. for 5 years with no loss of activity. Solutions of the enzyme prepared, aliquoted, and stored at −20° C. are stable for 6 months provided they are thawed and refrozen a minimum number of times. Collagenase exhibits excellent stability at 4° C. and 22° C., whereas temperatures above 56° C. completely inactivate the enzyme.

Commercially available collagenase exhibits differences in enzyme activity and purity between batches; accordingly, some lots are more effective than others for the solubilization of prostatic tissue. Commercial preparations of bacterial collagenase are often accompanied by small amounts of contaminating proteases, peptidases, mucopolysaccharidases, and glycosidases including: clostripain, trypsin, and a caseinase-like amino-peptidase. Clostripain is the most abundant contaminating enzyme in crude collagenase preparations and contains an essential SH group, is activated by cysteine, and is inhibited by sulfhydryl binding agents. clostripain has a trypsin-like specificity. Crude collagenase preparations with small amounts of contaminating enzymes such as trypsin and clostripain are often more effective than highly purified preparations of collagenase, suggesting a possible combined action of the multiple enzymes or proteases aids in the solubilization of prostatic tissue.

Crude collagenase preparations are especially useful for prostatic tissue dissociation purposes when combined with other enzymes such as hyaluronidase, elastase, and trypsin. Only collagenase breaks down the collagen component of the connective tissue stroma enabling further proteolytic attack by other degradative enzymes such as trypsin. The extracellular matrix that holds cells together is a complex mixture of proteins, glycoproteins, lipids, glycolipids, and mucopolysaccharides. Treatment of prostatic tissue with solutions of crude bacterial collagenase in combination with hyaluronidase, results in extensive digestion of the prostatic extracellular matrix due to the wide variety of proteolytic activities present in such mixtures.

Advantages obtained in the use of collagenase for the dispersal or dissolution of prostatic tissue are believed due, in part, to its high specificity. Collagenase may be incubated for longer times, at higher concentrations, and provide more extensive dissociation of tissue and organs rich in collagen than other proteolytic enzymes. Collagenase does not require the strict control of concentration and time of digestion as, for example, does the general proteolytic enzyme trypsin. Due to their powerful cell dispersive effects, bacterial collagenases are preferred for the digestion of the nodules of BPH, which are rich in collagen.

Collagenase digests through hydrolysis the stromal collagens I, II, III, basement membrane Type IV, and Type V collagen. In addition to stromal collagen, the basal lamina is one of the sites of collagenase activity when prostatic tissue is exposed to collagenase. As a result, epithelial cells separate from the underlying stromal components. Upon exposure to collagenase, stromal cells (fibroblasts) can be seen separating from the epithelium. The cells are partially digested and degenerating, which indicates a loss of viability. Undigested epithelial cells have a clean outer surface. Due to collagenase activity, the collagen of the lamina propria and of the remaining stroma is digested.

Collagenase is very effective in the dispersal of stromal and glandular components of the prostate into single cells. The glandular tissue is essentially stripped of all supportive stroma with disruption of the glandular structure itself accompanied by the interstitial solubilization of collagenous fiber bundles. Collagenase inhibits fibroblastic growth and shows some degree of cytotoxicity for fibroblasts.

The bacterial collagenase derived from *Clostridium hystolyticum* is readily available and has found wide application in a variety of laboratory and clinical applications. Early applications of collagenase involved cell dispersion techniques for tissue culture and demonstrated advantages over other enzymes for purposes of tissue disruption. The use of collagenase in medical practice is well known but has been, heretofore, limited to topical applications for debridement of burns or ulcers, for intervertebral discolysis, and in ophthalmic surgery. Clinical applications of collagenase have found wide acceptance in burn treatment centers. Collagenase, in conjunction with antibiotics, has been shown effective in the debridement of burns and to promote wound healing often without keloid formation. Collagenase may be useful in preventing or curing keloids. Collagenase has been incorporated into topical ointments for the treatment of dermal ulcers. Enzymatic debridement with collagenase has been clinically applied in necrotic conditions resulting from hot and cold cauterization of the cervix. Direct injections of collagenase have been used for intervertebral discolysis, the treatment of Peyronie's disease, and as an adjunct to cryoprostatectomy for the removal of retained cryo-slough.

Collagenase is antigenic; however, topical applications have not been found to elicit an immune response in patients treated for long periods of time with collagenase-based ointments. Bacterial collagenases have been shown to be nontoxic even though *Clostridium hystolyticum* is known to produce highly poisonous endotoxins. Collagenase of clostridial origin may require purification and removal of endotoxins prior to injection in humans.

Intravenous injections of collagenase have shown a very low degree of danger to experimental animals. In mice the IV LD-50 of crude collagenase has been shown to be 300 mg/kg body weight. Oral solutions of collagenase in water have been proven to be nontoxic at doses as high as 8,000 mg/kg body weight. The acute IV LD-50 in rats has been shown to be 1272 U/kg for collagenase.

B. Hyaluronidase

Hyaluronidase (Hyaluronate 4-glycanhydrolase) is an enzyme that digests hyaluronic acid and has been isolated from microorganisms and mammalian testes. Hyaluronidase derived from ovine testes, EC 2.1.1.35, is preferred. Enzymes with similar properties to the testicular hyaluronidase have been found in snake and bee venom, and in human tissues and serum. Hyaluronidase catalyzes the degradation of hyaluronic acid (an acidic mucopolysaccharide) into disaccharides, tetrasaccharides, or a mixture of both. The enzyme is a glycoprotein that hydrolyzes chondroitin sulfates A & C resulting primarily in the release of tetrasaccharides. Monosaccharides are not typically released.

Hyaluronidase activity has been demonstrated in a wide variety of microorganisms and in mammalian tissues and fluids. Hyaluronidase activity is linear with time, and enzymes from different tissue sources may exhibit different pH optima. Heparin, heavy metals, and strong polyanions inhibit hyaluronidase, whereas polycations tend to activate hyaluronidase.

Testicular hyaluronidase causes the random hydrolysis of 1,4 linkages between 2-acetamido-2-deoxy-$\beta$-D-glucose and D-glucuronate residues in hyaluronic acid. Inhibitors of hyaluronidase activity include: heparin, chondroitin sulfate B, heparin sulfate, polystyrene sulphonate (competitive inhibitors), bile salts, dyes, sulfated detergents, $Fe^{2+}$, $Fe^{3+}$, $Mn^{2+}$, $Cu^{2+}$, $Zn^{2+}$, $Mg^{2+}$ and specific antibodies. Testicular hyaluronidase has a molecular weight of 55,000 daltons and an absolute requirement for cations. $K^+$ and $Na^+$ cations have a greater effect than $Ca^{2+}$ ions. A 1% solution of hyaluronidase exhibits an extinction coefficient of 8 when measured at 280 nm. Hyaluronidase has an optimal pH ranging from 4.5 to 6 and is stabilized by the presence of NaCl.

Hyaluronidase derived from ovine testes is stable for 1 to 2 years when stored lyophilized at 4° C., and is stable in 0.02 M phosphate buffer for a few days at 4° C. Hyaluronidase preparations should exhibit an activity greater than 1000 units per mg of protein. No loss of activity is observed upon heating the enzyme for 60 minutes at 42° C.; 50% loss of activity is found after heating at 48° C. for 30 minutes; and 80% loss of activity is observed after heating the enzyme for 5 minutes at 100° C. EDTA appears to be a stabilizing agent.

Hyaluronidase appears to increase the permeability of connective tissue ground substance through direct enzymatic liquefaction. Hyaluronidase is suitable for the digestion of hyaluronic acid and chondroitin sulfate in connective tissues. Hyaluronidase is not pharmacologically toxic, increases osmosis, and is inhibited by steroids.

Hyaluronidase is an enzyme derived from mammalian testes. The enzyme has been used previously in human medicine to increase the effect of local anesthetics. Hyaluronidase hydrolyzes the hyaluronic acid part of connective tissue, forming glycosaminoglycans. The enzyme facilitates the absorption of injected fluids and the resorption of exudates. Hyaluronidase has been used to promote the absorption of relatively large injection volumes administered by the subcutaneous or intramuscular routes. Topical applications of hyaluronidase have been used in surgery to aid in the separation of abnormally adherent structures by weakening the fibrous connective tissue. Hyaluronidase has been shown to reduce the extent of myocardial infarct when administered within 8 hours of onset of the attack in man by the bolus intravenous injection of 500 NF units of hyaluronidase per kg of body weight every 6 hours for 48 hours.

In animals, the intravenous injection of 75,000 International Units of hyaluronidase results in no significant change in blood pressure, respiration, body temperature, or renal function. Hyaluronidase should not be injected into areas of known infection. Cases of sensitivity to hyaluronidase have been reported. Hyaluronidase, upon repeated injection, may elicit an immune response and result in the formation of specific antibodies which may inactivate the enzyme or become localized in the testes causing testicular degeneration.

The combination of hyaluronidase and collagenase is a preferred enzymatic composition of the invention. Collagenase derived from *Clostridium hystolyticum* is preferred, and hyaluronidase derived from ovine testes is preferred.

C. Other Enzymes

Trypsin, such as EC 3.4.21.4, is derived from the pancreas and is produced in an inactive form or zymogen. The inactive precursor of trypsin is called trypsinogen and is activated by small amounts of other proteolytic enzymes. Trypsin is a serine protease that hydrolyzes peptide bonds mainly between lysyl and arginyl amino acid residues in natural and synthetic substrates. Trypsin breaks down the proteins of the cell membrane, initiates cell dispersion through membrane damage, and is inhibited by a wide variety of proteinase inhibitors.

Trypsin is slow to dissociate the collagenous connective tissue of organs as the enzyme exhibits little or no activity toward the intercellular ground substance. Trypsin may promote a limited digestion of the terminal regions of the collagen molecule but is unable to digest the triple helical region, which composes over 95% of the collagen molecule. As a result, tissues rich in highly cross-linked collagen are difficult to disperse with trypsin alone.

Trypsin has been used as a therapeutic agent for the debridement of wounds, necrotic ulcers, abscesses, sinuses and fistulas. Due to the presence of trypsin inhibitors in serum, low concentrations of the enzyme do not typically attack living tissues. The enzyme has been employed as an ointment and as wet or dry dressings. Powdered trypsin may be sprinkled over wounds or inserted into cavities or fistulas by means of small gelatin capsules. Solutions of trypsin have been used as an aerosol for the liquefication of sputum in bronchial disorders. Oily suspensions of trypsin have been injected intramuscularly as an anti-inflammatory agent and in the treatment of bronchial asthma, bronchitis and thrombophlebitis.

Chymotrypsin, such as EC 3.4.21.1, is derived from the pancreas and is produced as an inactive precursor zymogen form called chymotrypsinogen. Activation of chymotrypsinogen may occur autolytically or by the action of trypsin and other proteases. The activation mechanism is complex. Chymotrypsin is inhibited by $\alpha$-1-antrypsin and $\alpha$-2-macroglobulin. A wide variety of molecules can act as substrates for chymotrypsin including synthetic esters and amides. The natural substrates of chymotrypsin hydrolysis involve preferential cleavage of peptide bonds in the $\beta$ position of the carbonyl group of the aromatic amino acids L-tryptophan, L-tyrosine, and L-phenylalanine.

Chymotrypsin has been used both orally and parentally for the prevention or treatment of local and systemic inflammation, for the dispersal of extravasated blood, and effusions. Therapy with this proteolytic enzyme has been reported to be effective in reducing inflammation due to a wide variety of causes including: fractures, surgical trauma, sports related injuries, accidental soft tissue trauma, in intervertebral disc lesions, and cataract surgery.

Heat denatured chymotrypsin is less toxic than the native enzyme. Chymotrypsin exhibits decreased toxicity when injected rapidly. Occasional anaphylactic reactions to chymotrypsin have been reported and intradermal or scratch testing is recommended for patients with a history of allergies.

Pronase, such as EC 3.4.24.4, is a registered trademark of Calbiochem/Behring, La Jolla, Calif. Pronase is a nonspecific mixture of several proteolytic enzymes derived from Streptomyces griseus K-1, including the neutral and alkaline proteases, amino-peptidases, and carboxypeptidases. The neutral proteinases hydrolyze peptide bonds containing the amino group of leucine, phenylalanine, and tyrosine. The alkaline proteases are similar in activity and specificity to pancreatic trypsin. Aminopeptidase and carboxypeptidase are metalloenzymes that are inhibited by EDTA. Pronase digests glycoproteins and releases glycopeptides at an optimal pH of approximately 7.5. Pronase is a broad spectrum protease that digests almost any protein to free amino acids.

Pancreatic Elastase, such as EC 3.4.21.36, is an endopeptidase that digests native elastin, the elastic fibrous protein in connective tissue, but not native collagen or keratin. Elastase is inhibited by NaCl and KCl and the proteinase inhibitors elastatinal, $\alpha$-1-antitrypsin, and $\alpha$-2-macroglobulin.

Elastases are endopeptidases (proteinases) that are capable of solubilizing elastin by proteolytic cleavage. Elastases are found in the pancreas, neutrophils, platelets, macrophages, spleen, aorta, skin, snake venoms, and in some microorganisms. Elastase derived from macrophages and microorganisms are metalloenzymes; all other elastases are serine proteases. Proelastase is an inactive elastase precursor zymogen that is activated by trypsin or enterokinase.

Elastase exhibits a broad specificity and is capable of digesting many other proteins in addition to elastin. This broad specificity complements the activity of other proteases such as trypsin and chymotrypsin. The broad substrate specificity also aids in the enzymes ability to digest elastin, which is a highly cross-linked fibrous protein trypsin and chymotrypsin have such a narrow specificity that they are unable to cleave enough peptide bonds to dissolve the net-like structure of elastin by themselves.

Elastase is a serine protease with a specific hydrolytic activity for elastin in addition to its activity for the nonspecific hydrolysis of various amides and esters. Elastase catalyzes the hydrolysis of peptides (especially at bonds adjacent to neutral amino acid residues) including elastin, denatured collagen, fibrin, albumin, hemoglobin, and casein. Elastase is capable of digesting a number of connective tissue components including: proteoglycans, fibronectin, and Type III collagen. Elastases are also capable of digesting fibrinogen and histones. The broad substrate specificity of elastase combined with its activity at physiological pH provide the enzyme with a great potential for causing extracellular damage.

Dispase, such as EC 3.4.24.4, may be suitable for the disintegration of tissues for cell culture purposes. Dispase is gentle (does not damage cell membranes during one-hour incubations), is stable to temperature, pH, and interference from serum components. Dispase is similar in properties and substrate specificity to thermolysin. Dispase has been used for the dissociation of many types of tissue including thyroid, pancreas, and endothelial cells of blood vessels.

Deoxyribonuclease, DNase I, EC 3.1.21.1, is an endonuclease derived from bovine pancreas. DNase hydrolyzes native, highly polymerized DNA and denatured DNA. DNase does not hydrolyze RNA. DNase I preferentially attacks the linkages between adjacent purine and pyrimidine nucleotides. DNase I splits the phosphodiester bonds adjacent to pyrimidine nucleotides and acts upon single stranded DNA, double stranded DNA, and chromatin. Although histones tend to inhibit the activity of DNase, over time, all chromatin DNA may be digested. DNase is inhibited by actinomycin D, ethidium bromide, and EDTA. Fluoride, citrate, arsenate, borate and selenite ions inhibit DNase activity due to their ability to remove essential $Mg^{2+}$.

Plasmin, such as EC 3.4.21.7, is a proteolytic enzyme that dissolves fibrin and is derived from plasminogen when activated by streptokinase. Plasmin has fibrinolytic activity and has been used for the treatment of thrombotic disorders, as an adjunct to anticoagulant therapy and for the debridement of wounds when used in conjunction with DNase. Plasminogen activator is a neutral protease secreted by mononuclear phagocytes during inflammatory responses. Plasminogen activator is thought to mediate extracellular protein degradation by macrophages in the presence of plasminogen.

Surfactants

The present enzyme composition also preferably includes a surfactant to aid in the solubilization and lysis of prostatic tissue. Nonionic surfactants, such as alkyl-phenyl-polyoxyethylene surfactants, have been found to be particularly useful. Triton® X-100, octyl-phenoxy-polyethoxyethanol, an octylphenyl polyoxyethylene oxide commercially available from Rohm and Haas, Philadelphia, Pa., is an example of a preferred surfactant.

Lipids are a major component of prostatic fluid and cells. Phospholipids, cholesterol and cephalin account for most of the lipids present in prostatic secretions. The prostatic glandular or epithelial cells are responsible for the synthesis of a large proportion of the cholesterol and phospholipids found in prostatic secretions. Prostatic fluid cholesterol levels are elevated in BPH. Treatment of prostatic tissue with mild detergent solubilizes the phospholipids of cellular membranes and emulsifies the cholesterol of prostatic fluid. Nonionic alkyl-phenyl-polyoxyethylene surfactants have been found particularly effective in aiding the enzymatic hydrolysis and solubilization of prostatic tissue.

Nonionic surfactants are molecules that are partially hydrophobic and partially hydrophilic, resulting in an agent that is effective in solubilizing membrane lipids. The solubilization of membranes generally proceeds in stages: the detergent is bound to the membrane; the membrane is lysed; and the membrane is solubilized in the form of lipid-detergent-protein micelles, lipid-detergent micelles, and protein-detergent micelles. The solubilization of membrane proteins may occur at any of these stages described. Some proteins are selectively extracted before the membrane is disrupted and are found mainly as protein-detergent complexes. Most of the membrane proteins are solubilized as the membrane breaks up resulting mainly in lipid-protein-detergent complexes. Several factors may affect the performance of detergents including pH, temperature, ionic strength, and detergent concentration.

Triton® X-100 (octylphenoxy polyethoxyethanol) is a nonionic surfactant comprised of octylphenol condensed with 8 to 10 moles of ethylene oxide and is reported to have a chemical formula of $C_{14}H_{22}O(C_2H_4O)_n$ where $n=8-10$. The compound is a slightly turbid viscous liquid, miscible with water, and has a specific gravity of 1.07. Triton® X-100 is composed of extremely hydrophobic molecules (those with short polyoxyethylene chains) that bind tightly to the hydrophobic regions of proteins. Triton® X-100 has a phenyl group which strongly absorbs UV light in the 260 to 280 nm range. Triton® X-100 is supplied as a viscous liquid of essentially pure detergent which has been purified to reduce the peroxide contamination. Viscosity increases as temperature decreases and handling becomes difficult below 20° C.

Triton® X-100, a polyoxyethylene derivative, breaks up the lipid bilayer of cellular membranes separating the lipids from the membrane proteins. Nonionic detergents, such as Triton® X-100, displace the lipids that normally associate with the hydrophobic proteins of the membrane. The solubilization is gentle resulting in the maintenance of subunit structures of the membrane proteins and in the retention of enzyme activity or function. The detergent does not generally break up protein-protein interactions.

Nonionic surfactants have been used in a number of biologic situations and have been shown to be useful in maintaining perfused organs in a functional state for limited time periods. Additionally, these compounds have been found to enhance cellular growth in tissue culture, stabilize fat emulsions for intravenous administration, prolong the safe storage period for blood and to prevent fat embolism and hemolysis during extracorporeal circulation.

Triton® X-100 and NP-40 are mild nonionic detergents that have been shown to be effective in the solubilization and extraction of lipid containing nuclear and cellular membranes. Complete solubilization of lecithin bilayers has been demonstrated with Triton® X-100 at a working ratio of approximately 2:1 (detergent:phospholipid). Solubilization of membrane proteins (production of lipid free detergent-protein micelles) may require more than 10 mg Triton® X-100/mg of membrane lipid.

Highly active tissue collagenases and PMN leukocyte collagenases have been prepared by tissue dissociation techniques involving homogenization of tissue in 0.25% Triton® X-100 (in 0.01 M $CaCl_2$) and 0.05% Triton® X-100 (in 0.05 M Tris; pH 7.5, containing 0.15 M NaCl and 0.01 M $CaCl_2$) respectively. The recovery of collagenase from tissues is markedly enhanced if the detergent Brij 35 (polyoxyethylene lauryl ether) is incorporated throughout the purification procedure.

Triton® X-100 toxicity data indicate a slight to moderate hazard exists following ingestion which may lead to nausea and vomiting. The detergent may be a mild irritant to sensitive skin and cause severe eye irritation with symptoms of inflammation, tearing, and possible corneal damage on acute contact. The LD 50 of Triton® X-100 given orally to rats is 1800 mg/kg. The rabbit dermal LD 50 is over 3000 mg/kg.

Triton® X-100 has properties that are similar to a number of other alkylphenyl polyoxyethylene detergents, such as Triton® X-114. Many of the nonionic detergents are polyoxyethylene or polyoxypropylene derivatives, and are available in a variety of molecular weights and differing physical properties.

Suitable, mild, nonionic surfactants that have been shown to be effective in the solubilization and extraction of lipid containing nuclear and cellular membranes include the condensation products of ethylene oxide with partial fatty acid esters of sorbitol and sorbitol anhydride. These surfactants are commercially available as the Tween® series (Atlas Chemical); wherein, the molar ratio of ethylene oxide to alcohol is within the range of about 15:1 to 25:1 with the fatty acid component comprised of laurate, stearate, or oleate ($C_{10}$–$C_{20}$).

Other nonionic surfactants that may be employed in the present composition include the ethylene oxide esters of $C_6$–$C_{12}$ alkyl phenols such as nonylphenoxy polyoxyethylene ether. Particularly useful are the esters prepared by condensing 8 to 12 moles of ethylene oxide with nonylphenol. Commercially available detergents of this type include the Igepal CO series (GAF Corp.).

Additional useful nonionic surfactants may include the condensation products of ethylene oxide with a hydrophobic polyoxyalkylene base such as propylene oxide condensed with propylene glycol. Compounds of this type include the commercially available surfactants Pluronic F-127, Pluronic PX, and Pluronic L-62 (Wyandotte Corp.).

Further useful nonionic surfactants include the condensation products of $C_8$–$C_{22}$ alkyl alcohols containing 2 to 50 moles of ethylene oxide per mole of alcohol. Detergents of this type include the condensation products of $C_{10}$–$C_{20}$ fatty alkyl alcohols containing 3 to 45 moles of ethylene oxide per mole of alcohol. These compounds are commercially available as the Poly-Tergent SLF series (Olin Chemicals) or the Tergitol series (Union Carbide).

Triton® X-100 is a nonionic surface active agent and is effective as an emulsifier, wetting agent, and detergent. Examples of other commercially available polyoxyalkylene-based nonionic surfactants include: Triton® X-114 (Rohm & Haas), Tween® 20/80 (Atlas Chemical), Genapol X-080/100/150, C-100 (Hoechst AG), Thesit (Destin-Werk GMBH), Brij 35, Lubrol PX (ICI Americas), Pluronic F-127 (Wyandotte Chemicals Corp.), Nonidet P-20/40 (Shell Oil Corp.), Igepal CO-630/710 (GAF), Surfonic N-95 (Jefferson), Tergitol NP-27 (Union Carbide).

Surfactants are preferably added to the present composition at a concentration of about 0.1% to 10% by volume of the composition. More preferably, surfactants are present in the composition at a concentration of about 0.5% to 5% by volume.

Antibiotics

Direct injection of the prostate is generally a safe, simple, and effective means of introducing the present composition directly into the body of the enlarged prostate in order to cause the solubilization and regression of obstructive prostatic tissue. Direct intraprostatic injection avoids the potential problem of metabolic inactivation of the enzymatic components of the composition, while allowing the composition to be placed directly at the desired site of action. However, intraprostatic injection techniques may be associated with the risk of acquiring bacterial infection that may lead to complications such as post-injection fever, bacteriuria, and bacteremia.

Prostatic infections are generally due to one of the common gram-negative urinary tract pathogens with therapy guided by the antibiotic sensitivity pattern of the infecting strain of bacteria. The causative organisms of bacterial prostatitis include: *Escherichia coli;* species of Proteus; Klebsiella, Enterobacter, Pseudomonas, Serratia; and other less common gram-negative organisms. Most prostatic infections are caused by a single pathogen; however, infections involving two or more strains of bacteria occur occasionally. Gram-negative coliform bacteria are the most frequent cause of bacterial prostatitis.

It is preferred that the present enzyme composition include a suitable antimicrobial agent to prevent or reduce the incidence of bacterial infection that may be associated with the present injection method. Antibiotics used should provide adequate protection against the commonly encountered bacterial strains of uropathogens including: *Escherichia coli, Streptococcus faecalis,* Proteus/Pseudomonas spp. and coagulase-positive Staphylococcus. The antibiotic selected should not substantially inhibit the enzymatic activity of the composition.

Gentamicin sulfate (Garamicin®) commercially available from Schering Corp. (Kenilworth, N.J.), and trimethoprim/sulfamethoxazole (Septra®), commercially available from Burroughs Wellcome (Research Triangle Park, N.C.), exhibit the appropriate spectrum of activity against the bacteria which cause urinary tract infections, yet do not interfere or inhibit the activity of collagenase and hyaluronidase, and are thus preferred. Garamicin® is a water soluble aminoglycoside which exhibits activity against a wide variety of pathogenic gram-negative and gram-positive bacteria including: *Escherichia coli,* Proteus species (indole positive and indole negative), *Pseudomonas aeruginosa,* species of the Klebsiella-Enteroacter Serratia group, Citrobacter species, and Staphylococcus species (including penicillin and methicillin resistant strains). Septra® is indicated for the treatment of urinary tract infections due to susceptible strains of the following organisms: *Escherichia coli,* Klebsiella-Enterobacter, *Proteus mirablis, Proteus vulgaris,* and *Proteus morganii.*

Gentamicin has been demonstrated to be of value in the prophylaxis of bacterial infection in patients undergoing prostatectomy. A single dose of gentamicin (3–5 mg/kg), given intramuscularly two hours before surgery, was the most effective in reducing the incidence of post-operative bacteriuria. Single-dose therapy is less expensive, less likely to lead to problems of superinfection, resistant strains, and toxicity. Additionally, it has been demonstrated that short-term prophylaxis does not modify the normal fecal flora as opposed to long term treatment regimens. Other antibiotics given as a single pre-operative prophylactic dose may prove equally effective.

Trimethoprim is a lipid-soluble base with limited binding to plasma proteins, and typically shows prostatic tissue: serum levels of 2:1 to 3:1. Trimethoprim/sulfamethoxazole (TMP/SMX) produces therapeutic levels in the urine and prostatic secretions with an appropriate antibacterial spectrum of activity. Recommended therapy with TMP/SMX involves dosages of 160 mg TMP and 800 mg SMX, orally twice a day for 30 days. Should TMP/SMX not be tolerated (allergies), gentamicin therapy is recommended.

Generally, the antibiotic is present in the composition at a concentration of about 0.15 to 150 $\mu$g/ml. The preferred antibiotic, gentamicin sulfate, is present in the composition at a concentration of 1.5 to 150 µg/ml, preferably 10 to 25 µg/ml. Alternatively, for those patients who may be allergic to aminoglycosides in general, and gentamicin in particular, the combination drug trimethoprim/sulfamethoxazole may replace gentamicin as the preferred antibiotic of the present claimed composition. Trimethoprim is preferably present at a concentration of 1 to 10 µg/ml, more preferably 5 to 10 µg/ml. Sulfamethoxazole is preferably present at a concentration of 30 to 105 µg/ml, more preferably 50 to 105 µg/ml.

Antibiotics usually relieve the symptoms of acute prostatic infections promptly. However, no antimicrobial agent is effective against all pathogenic urinary tract microorganisms. Each has its own spectrum of activity against one or a variety of species. The best therapeutic agents for curing bacterial prostatitis are: highly lipid soluble; possess basic pKa; show minimal binding to plasma proteins; and are bactericidal against the common gram negative uropathogens.

Many antibiotics are of limited value in treating chronic infections of the prostate. The relative ineffectiveness may be due in part to the poor penetration of most antibiotics into the prostate, because the prevailing low pH of the prostate inhibits the solubility of these drugs. However, reports of remarkable success in curing bacterial prostatitis involve direct injection of antimicrobial agents into the prostate. Nearly all cases of chronic bacterial prostatitis can be cured by direct injection methods if the injections are repeated regularly.

Various antibiotics which have been shown to be effective against the common pathogens responsible for urinary tract infections include: gentamicin, trimethoprim/sulfamethoxazole, nitrofurantoin, nalidixic acid, tobramycin, amikacin, and netilmicin sulfate. Currently, the combination of trimethoprim/sulfamethoxazole is the drug of first choice in the treatment of bacterial prostatitis. Recent studies have indicated that a single dose of gentamicin, trimethoprim/sulfamethoxazole, or netilmicin sulfate is as effective as longer treatment in the prevention of postoperative bacterial urinary tract infections.

The preferred antibiotics of the present claimed composition, gentamicin or trimethoprim/sulfamethoxazole, may be selected from the groups of antibiotics which exhibit the appropriate spectrum of activity against the commonly encountered bacterial strains of uropathogens including: penicillins (penicillin G, penicillin V, benzathine penicillin); amino penicillins (ampicillin, amoxicillin); carboxy penicillins (carbenicillin, piperacillin, mezlocillin); penicillinase resistant penicillins (methicillin, oxacillin, nafcillin); cephalosporins (cephalexin, cephalothin, cefotaxime, cephazolin); aminoglycosides (streptomycin, neomycin, kanamycin, tobramycin, amikacin, netilmicin, sisomicin); tetracyclines (doxycycline, minocycline, tetracycline), polymyxins (polymyxin B & E); sulfonamides (sulfisoxazole, sulfasuxidine); fluoroquinolones (ciprofloxacin, norfloxalin); basic macrolides (erythromycin, oleandomycin); lincomycin; clindamycin; chloramphenicol; nitrofurantoin; and nalidixic acid.

Method of Delivery

The present invention discloses an aqueous parenteral composition that, in one of the preferred embodiments, contains a therapeutically effective amount of the enzymes collagenase, hyaluronidase, the detergent Triton® X-100, and the antibiotic gentamicin. The invention also provides a method of delivery such that direct intraprostatic injection of therapeutically effective amounts of the disclosed composition results in the relief of the obstructive symptoms associated with BPH. Intraprostatic injections are accomplished by means of a long, fine needle inserted into the prostate under digital rectal control and/or ultrasonic guidance. The injections are usually done under local anesthesia. The injection solution may be diluted with lidocaine. During the injection, the needle may be frequently relocated in order to obtain the best possible distribution of the composition. Several routes of injection are available for the introduction of the disclosed composition into the prostate.

The preferred route of administration is by means of transurethral intraprostatic (intralesional) injection. The transurethral technique is immediately preceded by catheterization. The volume of the composition injected typically varies from 1 to 20 cc/lobe. To optimize the solubilizing effects of the injected composition, it may be desirable to dilate the prostatic urethra with an inflatable balloon. The cystoscopically inserted balloon inhibits the immediate egress of the injected enzyme solution through the porous duct system that empties into the urethra. Inflation of the balloon may also provide a physical means of relieving the prostatic encroachment and aid in remolding the softening, solubilizing prostatic tissue. The advantage of this route of injection is that the method allows for direct cystoscopic visualization of the nodular areas of pathology and for the placement of a high concentration of the composition at the desired location without the risk of metabolic inactivation. The pain and discomfort experienced by patients during direct injection of the prostate typically are minimal and comparable to intramuscular injections.

Alternatively, the transperineal or transrectal routes of prostatic injection may be used. The transperineal route of injection involves the placement of 22 g×20 cm aspiration biopsy needle through the perineum into the prostate guided by ultrasound and/or digital palpation. Again, 1 to 20 cc of the disclosed composition is typically injected into each lateral lobe of the prostate. The injections are generally done under local anesthesia. During injection, the needle is frequently relocated to obtain the best possible distribution of the composition. The position of the needle may be guided by ultrasound while kept under constant digital rectal control. The transperineal route of injection may be a better alternative than either the transurethral or transrectal routes in terms of reducing potential complications due to post-injection bacterial infection.

In order to reduce the incidence of bacterial infection that may be associated with transperineal intraprostatic injection, aseptic injection techniques are recommended and are well known to those skilled in the art. Any one of a variety of standard bactericidal preparations such as Phiso-Hex®, Betadine®, povidone-iodine, or chlorhexidine applied to the skin of the perineum provides adequate pre-injection antibacterial protection. With sterile urine, adequate skin preparation, and sterile technique, the entire procedure should have a low rate of infectious complication.

The transrectal route allows needle introduction through the rectal wall and injection of the prostate while performing digital rectal palpation. Injection via the transrectal route is performed with a slightly curved 22 g×20 cm flexible aspiration biopsy needle. The use of a Franzen needle guide (Precision Dynamics, San Fernando, Calif.) allows the needle to be safely directed into a suspected lesion under ultrasonic and/or tactile guidance techniques. The sterilized prostate needle guide is placed on a gloved index finger. A finger cot is placed over the needle guide. The index finger and needle guide are inserted into the rectum and suspected lesions of the prostate are palpated. The needle is inserted through the guide and advanced into the tissue. Approximately 1 to 20 cc of the solution may be injected into the lateral lobes of the prostate. In order to inject sufficient material, the needle may be moved back and forth three to five times. An anesthetic jelly may be applied before injection to reduce pain during needle puncture.

Upon injection, the prostatic lobe swells, increases in size, and becomes turgid. Injected fluid forced through the veins at the site of injection may induce wide spread venospasm associated with microinfarcts. Acute urinary retention may occur in the immediate post injection period. Fluid injected into the prostate fills the alveoli of the gland at the site of injection and may rupture through the walls of adjacent alveoli entering the prostatic urethra via the alveolar ducts. As much as ⅓ to ½ of the injected fluid may ultimately reach the prostatic urethra.

The bolus injection of more than 5 cc of the composition into the body of the in situ prostate may result in reflexive smooth muscle contraction causing the therapeutic enzyme solution to be rapidly emptied through the porous ducts, away from the target tissue, and into the urethra. The force of the injection may cause rupture of prostatic tissue at the site of injection. The injected fluid may gain access to the ducts of the glandular alveolar system and completely fill the gland. Once the gland is filled, the fluid takes the path of least resistance and flows to the urethra.

Injection fluid may gain access to the prostatic circulation and be responsible for scattered minute areas of infarction. Enzyme induced thrombophlebitis of the veins may be responsible for the appearance of widespread hemorrhagic infarctions. About ⅕ of the prostatic injection fluid may enter the general circulation as demonstrated by experiments involving excretion of methylene blue by the kidneys. The subcapsular and periurethral zones of the prostate are more vascular in nature and may enhance the flow of the fluid into the blood stream. Injections of India ink carbon particles into the prostate resulted in no gross or microscopically detectable particles in the lymphatics of the pelvis. Prostatic injection fluid may also reach the surface of the prostate and periprostatic tissue through the point of needle entry. Radiographs taken immediately after intraprostatic injection of radio-opaque microemulsions of barium sulfate have shown fluid leakage beneath the prostatic capsule and escape into the bladder. Occasionally, the fluid has been seen to leak outside the capsule as well.

The injected lobule of the prostate undergoes necrosis mainly due to the enzymatic action of the injected composition and partly due to the shear force of the fluid injected under pressure. Part of the fluid that leaks back through the point of needle entry may cause thrombosis of surface vessels and be responsible for adhesions with adjacent viscera. The quantity of fluid that leaks back depends upon the local pressure and is likely to increase with the force of the injection. Injected fluid passing through the periurethral veins may cause their inflammation and thrombosis which in turn may result in necrosis and sloughing of the urethral epithelium.

Urethral and periurethral solubilization is expected to occur around the entire circumference of the prostatic urethra which may lead to denudation of the urethral epithelium. Histopathologic changes associated with injection of the tissue solubilizing enzymes include those due to fluid escape along ducts of the gland resulting in damage to the ducts and surrounding alveoli. The fluid that leaks back through the point of needle entry may affect the capsular vessels and smooth muscle fibromuscular stroma situated there.

Direct localized injection of the prostate results in a high concentration of therapeutic enzymes at the very focus of the problem without the risk of metabolic inactivation. However, intraprostatic injections during acute exacerbations of infection are not recommended because of the danger of general dissemination of the infection and possible septicemia. Hematuria and hemospermia may be present for some weeks following the injection.

Depending upon the patient being treated, the therapeutically effective dose of the composition administered may range from 1 cc to 20 cc containing 160 to 160,000 U/ml hyaluronidase, 250 to 250,000 U/ml collagenase, 0.1 to 10% Triton® X-100, and 1.5 to 150 µg/ml gentamicin. These dosage ranges represent quantities of the various components of the composition that are estimated to be therapeutically effective in providing relief from the obstructive symptoms associated with benign prostatic hypertrophy. However, the dose of the composition may vary depending on the age of the patient, nature and severity of disease, potency of the composition, and route of administration. Treatment regimens encompassed by a preferred embodiment of the present invention employ the intraprostatic injection of safe and effective amounts of the preferred composition in order to cause the solubilization and regression of obstructive prostatic tissue. The injections may be administered in daily, weekly, or monthly injection protocols until the therapeutically desired result is obtained.

Other Methods of Delivery

If problems are encountered that limit or inhibit the therapeutic effects of the present composition, alternative means of delivery may be used. For instance, the effectiveness of enzyme therapy may be limited by the short circulating half-lives of exogenously administered enzymes, by the development of immunological responses to foreign protein, by inhibition from antiproteinase effectors ($\alpha$-1-antitrypsin, $\alpha$-2-macroglobulin), or by the inability to specifically target the enzymes to nodular areas of pathology.

A number of different carrier systems may be utilized to carry the enzymatic composition to the desired site in the prostate. In general, a suitable carrier should guide the therapeutic agent to its target without loss of specificity or reactivity. The carrier is preferably capable of linkage with the therapeutic enzymes and remaining as a complex until delivery is completed. The carrier preferably avoids triggering the immune defense mechanisms resulting in biodegradation or inactivation of the present composition.

The composition may be administered as a depot formulation that permits sustained release, prevents access to general circulation, and increases the prostate-specific localization of the composition. Such a formulation may be provided as a slow release implant, be microencapsulated, or attached to a biodegradable polymer or a prostate-specific immunoglobulin.

The use of antibodies as an enzyme composition carrier system may be desirable. The use of antibodies as carrier systems for the delivery of therapeutic agents to specific tissues exploits the antibody's unique ability to recognize and bind to targeted antigens. Also, antibodies carrying therapeutic reagents can be more effectively localized in tissues that are highly vascular in nature or are undergoing neovascularization. Additionally, cocktails of immuno-enzyme conjugates recognizing different cell types with different specificities may be useful.

Tissue specific monoclonal antibodies may be produced which better define the antigenic cellular targets to be localized. The use of F(ab) or F(ab')$^2$ fragments may improve localization properties. Antibodies containing the F(c) fragment tend to be specifically localized over a longer time period than F(ab) or F(ab')$^2$ fragments which exhibit accelerated clearance mechanisms. The recent development of human-mouse (chimeric) monoclonal antibodies may have therapeutic applications and provide advantages over conventional monoclonal antibodies of murine derivation. Human-mouse antibodies exhibit a wide range and high degree of specificity. Chimeric antibodies are less likely than conventional mouse monoclonal antibodies to elicit an immune reaction when injected into humans. The preparation and use of human monoclonal antibodies as carriers may further reduce the degree of immune response in the recipient to the introduction of foreign proteins. The antiglobulin response may also be controlled by such factors as method of antibody preparation, dosage, and route of injection.

The purpose of immuno-targeted enzyme therapy is to deliver an effective concentration of enzymes to a tissue specific site of activity, reduce toxicity to nearby normal tissues, and thereby increase the therapeutic index. Enzymes may be coupled to monoclonal antibodies that bind the enzyme covalently yet do not affect the enzyme's catalytic activity. Enzymes, which are coupled to tissue specific monoclonal antibodies, may be able to achieve a higher degree of specific localization in the targeted tissue, than native enzymes while maintaining their proteolytic activity.

Other specific localization concepts include zymogenantibody conjugates (trypsinogen) or enzyme-antibody conjugates (collagenase, hyaluronidase, elastase, DNase) which retain both enzyme and antibody activity. Enzymes may be encapsulated in lipoprotein, red blood cell (RBC) ghosts, polylactic acid, and other biodegradable membranes or synthetic microcapsules containing prostate-specific antibodies in order to increase and maintain specific targeting, localization, and activity of the solubilizing proteases in prostatic tissue.

The administration of collagenase and hyaluronidase may have immunologic consequences as repeated injections may result in the development of antibody titers and the accompanying risk of anaphylaxis or other less serious hypersensitivity reactions. Additionally, the presence of specific antibodies to collagenase or hyaluronidase may inhibit enzyme activity. Potential immunologic problems could occur if the active enzyme is recognized as foreign by the recipient's immune system. Antibodies may be produced against the enzymes and inactivate or precipitate the enzyme. Use of enzymes of human origin or those produced by recombinant techniques may minimize these potential immunologic complications.

Strategies that avoid the immune surveillance system involve methods of entrapment of enzyme preparations in biodegradable vesicles which protect the enzyme activity yet facilitate specific delivery. Targeting to specific sites of cellular pathology may be accomplished by attaching tissue specific proteins (monoclonal antibodies) to these vesicles. Enzymes may also be encapsulated in liposomes or other biodegradable microcapsules and subsequently attached to tissue specific monoclonal antibodies for specific localization purposes.

Liposomes are small spheres of concentric phospholipid bilayers containing an aqueous phase and have been shown to be useful as carrier systems. Current liposome preparation techniques permit the incorporation of a variety of drugs, hormones, or enzymes into either phase. Monoclonal antibodies may be incorporated into the outer layers of liposomes and provide increased specificity of delivery for the liposome contained therapeutic agent.

The entrapment of enzymes in synthetic microcapsules or biodegradable vesicles may provide a valuable method of specific delivery in addition to protecting the enzyme from physiologic inactivation and preventing immune complications. Various forms of membrane encapsulation techniques are available for the entrapment of enzymes including: erythrocyte ghosts; synthetic polymeric microcapsules; and lipid vesicles (liposomes) composed of cholesterol, lecithin, and phosphatidic acid. Use of the recipients own erythrocytes to deliver active enzyme may avoid the potential immunologic and physiologic problems resulting from enzyme administration in synthetic carriers (liposomes, microcapsules).

The covalent attachment of polyethylene glycol (PEG) to enzymes renders these proteins nonimmunogenic, may extend their circulating half-life, provide a means of escape from inhibition by naturally occurring enzyme inhibitors, and may result in enhanced enzyme activity with decreased autodigestion. The attachment of PEG to proteins is simple and yields homogeneous reaction products which may be purified by ultrafiltration.

Preparation and Testing of Composition

The present invention discloses as a preferred embodiment an aqueous composition containing a safe and therapeutically effective concentration of the hydrolytic enzymes collagenase and hyaluronidase, the detergent Triton X-100, and the antibiotic gentamicin for direct injection into the hyperplastic nodules which form in benign prostatic hypertrophy. It is preferred that the disclosed composition be prepared as a relatively concentrated solution of hydrolytic enzymes in a relatively small volume. Small volumes of safe and effective concentrations of hydrolytic enzymes are more readily placed and more efficiently digest the pathologic lesions of BPH, over time, than large volumes of relatively dilute solutions.

It is preferable that the claimed composition be provided in a unit dosage form suitable for intraprostatic injection. The composition may be administered to the patient as an injectable dosage of a solution or suspension of the compounds in a physiologically acceptable liquid diluent, such as pyrogen-free saline. For example, vials containing a lyophilisate of the composition may be prepared such that a sterile aliquot of the composition may be reconstituted and withdrawn as a pharmaceutically acceptable aqueous solution for injection into living mammals. The dose required for the composition to be therapeutically effective in patients with BPH may range from 1 cc to 20 cc. A preferred unit dose contains 250 to 250,000 U/ml collagenase, 160 to 160,000 U/ml hyaluronidase, (U=units) 0.1% to 10% nonionic surfactant, and 0.15 to 150 $\mu$g/ml antibiotic, most preferably a unit dose contains 2,500 to 25,000 U/ml of collagenase and 1,600 to 16,000 U/ml of hyaluronidase, 0.5 to 5% nonionic surfactant, and 15 to 150 $\mu$g/ml antibiotic.

Compositions of the present invention were prepared. Collagenase (Sigma Chemical Co., St. Louis, Mo.) and hyaluronidase (Boehringer/Mannheim Corp., Indianapolis, Ind.) were obtained as lyophilisates and reconstituted with citrate buffered saline containing 20 mN $CaCl_2$ (CBSCa) to the desired concentration. Collagenase, obtained from *Clostridium hystolyticum,* was chromatographically purified and contained small contaminating amounts of the enzymes clostripain, trypsin, and caseinase. Hyaluronidase, obtained from ovine testes, was also purified chromatographically. All enzyme activities were expressed as international units per mg.

The enzymes are stable when stored as lyophilisates at 4° C. However, access of moisture to lyophilized enzymes should be prevented. For example, cold vials of lyophilized enzyme should first be warmed to room temperature before being opened. Dilute reconstituted solutions of enzymes should be stored at 4° C., protected from light, and placed in an ice-bath when working at the bench.

Freshly distilled, deionized, sterile water is preferred for the reconstitution of enzymes and preparation of buffers used for injectable solutions. In the preferred embodiment, the buffer solution used is 0.05 M citrate buffered saline (CBS, pH 6.7), containing an adequate amount (preferably 0.01 M to 0.05 M, more preferably 0.02 M to 0.05 M) of calcium ions to activate the collagenase. It is recognized that any suitable buffer solution such as Ringers saline or tris buffered saline may be used. However, the buffer should contain sufficient calcium ions to activate collagenase, and should not contain calcium chelators such as EDTA or other inhibitors of enzyme activity such as cysteine.

The preferred buffer should exhibit a physiological pH which may range from about 6.5 to 7.5, with pH 6.7 to 7.0 preferred. The saline, e.g., sodium chloride, concentration is preferably about 0.1 M to 0.2 M with about 0.15 M to 0.2 M most preferred. Similarly, the concentration of citrate is preferably about 0.02 M to 0.1 M with 0.05 M to 0.1 M most preferred.

A preparation of 0.05 M CBS+20 mM $CaCl_2$ (pH 6.7) is composed of 550 mg sodium citrate, 190 mg NaOH, and 876 mg NaCl dissolved in 100 ml sterile, pyrogen-free, deionized $H_2O$. The solution was adjusted to a pH of 6.7 with 3 ml of 1 N NaOH, and 294 mg $CaCl_2$ was added. The surfactant Triton® X-100 (Malinckrodt, Paris, Ky.) and the antibiotic gentamicin (Sigma Chemical Co.) were added so as to obtain appropriate final concentrations. Triton® X-100 exhibits a density of 1.082 g/ml at 20° C. (924 $\mu$l/g at 20° C.). Gentamicin is included so as to obtain a final concentration of 150 $\mu$g/ml by adding 1.5 ml of a 10 mg/ml (15 mg) sterile solution of the antibiotic to 100 ml of the mixture.

The resulting solution is purified and sterilized by standard techniques. A solution (5 ml) of the enzymes collagenase and hyaluronidase (0.1% to 10%) in citrate buffered saline (pH 6.7) containing Triton® X-100 (0.1% to 10%), the antibiotic gentamicin (1.5 to 150 $\mu$g/ml), and $CaCl_2$ (20 mM) is prepared in pyrogen-free water, and passed over a 1 ml column (Detoxi-Gel®) to remove potential endotoxins. The final-step in the preparation of a pharmaceutically acceptable solution involves the passage of the composition through a certified sterile, nonpyrogenic microporous polysulfone filter with a pore size of 0.2 micrometer. Low protein binding filter membranes composed of polysulfones show significantly less protein absorption than comparable cellulose acetate/nitrate membrane filters. Filtration through a 0.2 mm sterile filter affords protection against contamination with microorganisms. Additionally, filtration minimizes the risks to patients posed by insoluble particulates or microaggregates.

Reconstitution and preparation of pharmaceutically acceptable solutions for parenteral use in humans is performed routinely in hospital pharmacies as standard practice. Solutions of collagenase/hyaluronidase/Triton® X-100/gentamicin (CHTG) in 0.05 M citrate buffered saline containing 20 mM $CaCl_2$ (CBSCa 6.7) ranging in concentration from 0.1% to 10% are stable for 2 weeks when stored at 4° C. and remain highly effective in solubilizing human and canine prostatic tissue. The toxicity of the composition is not believed greater than the toxicities of the individual components, which are known.

Collagenase (EC 3.4.24.3) derived from *Clostridium hystolyticum* was purchased from Sigma Chemical Company (Type XI, Product # C-7657, Lot Numbers: 96F-6801 and 96F-6838; Type XI-S, Product # C-4785, Lot Number: 17F-6814). Lot to lot variations of enzyme activity in terms of collagenase U/mg and levels of contaminating enzymes were observed and ranged from: 1910 to 2450 U/mg collagenase, 0.86 to 1.4 U/mg clostripain, 40 to 85 U/mg caseinase, and 0.05 to 0.52 U/mg trypsin.

One unit of collagenase activity is defined as the amount of collagenase which will release peptides from native collagen, equivalent in ninhydrin color, to 1 micromole of L-leucine in five hours at pH 7.4 at 37° C. in the presence of calcium ions. One unit of clostripain will hydrolyze 1 micromole of N-α-benzoyl-L-arginine ethyl ester (BAEE) per minute at pH 7.6 at 25° C. in the presence of 2.5 mM dithiothreitol. One unit of caseinase (nonspecific protease) will hydrolyze casein to produce color equivalent to 1 micromole (181 $\mu$g) of L-tyrosine in five hours at pH 7.5 and 37° C. (color by Folin-Ciocalteu reagent). One unit of trypsin activity will hydrolyze 1 micromole of N-α-benzoyl-L-arginine ethyl ester (BAEE) per minute at pH 7.6 and 37° C.

A. Collagenase Assay

The methods used to quantitate digestion of collagen by collagenase are generally based upon the detection of specific breakdown products of collagen or upon measurement of the disappearance of various species of macromolecular collagen. Azocoll® (a registered trademark of Calbiochem, Corp., La Jolla, Calif.) is a commercially available complex of particulate collagen and azo-dye. The complex is stable but treating it with a proteolytic enzyme liberates the dye in a soluble form. The unreacted Azocoll® can then be removed by filtration and the dye in the filtrate measured calorimetrically at 520 nm. Azocoll® is available in two mesh sizes, with the larger (50 to 100) preferred over the finer mesh (100 to 250) because the finer mesh material yields less color. Azocoll® is an excellent substrate for measuring collagenase activity because activity is proportional to time and concentration of the enzyme. The released dye can be measured with a visible colorimeter as opposed to a UV spectrophotometer, which is required for the Wunsch substrate. The Azocoll® assay permits rapid termination of the enzyme reaction by a one-step separation of enzyme and substrate by filtration through 1.2 to 5 $\mu$m porous membranes.

In order to quantitatively and reproducibly evaluate collagenase solutions for enzyme activity, a 10 mg/ml solution of Azocoll® is prepared in 0.05 M CBSCa 6.7. The assay consists of adding 1 ml aliquots of the Azocoll® suspension to 13×100 test tubes. The test solution (100 $\mu$l) containing collagenase is added to the test tubes with mixing and incubated for 15 minutes at room temperature. The reaction is quenched by adding 100 $\mu$l of 0.2 M EDTA (7.44 g/100 ml deionized $H_2O$). The entire reaction mixture is then filtered through a 1.2 micron Acrodisc® syringe filter (Gelman, Ann Arbor, Mich.) into plastic spectrophotometer cuvettes and the absorbance of the solution determined at 520 nm when blanked against 1 ml of CBSCa 6.7 containing 100 $\mu$l of 0.2 M EDTA. The assay is relatively linear with respect to collagenase concentration and is suitable for use on solutions ranging from 0.01% to 1%. Collagenase solutions containing 1% Triton® X-100 do not interfere with the Azocoll® absorption peak at 520 nm and increase collagenase activities by two fold. Triton® X-100 exhibits no activity toward Azocoll® over control backgrounds.

An alternative and more sensitive method for determining collagenase activity has been developed that involves the hydrolysis of a synthetic chromogenic substrate p-phenylazobenzyloxycarbonyl-L-prolyl-L-leucyl-glycyl-L-prolyl-D-arginine (PZC-PLGPA) with the colorimetric liberation of the yellow product p-phenyl-azobenzyloxycarbonyl-L-Pro-L-Leu spectrophotometrically determined at 320 nm. The alternative assay for the measurement of collagenase activity employs the synthetic chromogenic substrate (Wunsch) PZC-PLGPA. The reagent is prepared by dissolving 5 mg PZC-PLGPA into 1 ml of methanol followed by the addition of 4 ml of CBSCa 6.7. The method is suitable for determining collagenase activities in solutions ranging from 1% to 0.01% collagenase.

The Wunsch assay for collagenase is performed by adding to a 12×75 test tube 1 ml of PZC-PLGPA and a 100 μl sample of collagenase solution, and incubating for 15 minutes at room temperature with mixing. A sample of 100 μl of 0.2 M EDTA is then added with mixing (6 N HCl may substitute for EDTA). A 500 μl aliquot is removed and transferred to a 13×100 test tube containing 1 ml CBSCa 6.7 and 5 ml ethyl acetate. The mixture is vortexed for 15 seconds, an aliquot of the organic phase is transferred to tubes containing 350 mg $NaSO_4$. The absorbance is read at 320 nm vs. an air blank in glass cuvettes.

Collagenase is frequently measured in both Wunsch Units and in Mandl Units. There is no consistent conversion factor between the two units because the Mandl unit includes variable activities attributable to varying concentrations of contaminating proteases. Typical conversion factors are approximately 1 Wunsch U/mg to 1800 Mandl U/mg.

B. Hyaluronidase Assay

Hyaluronidase (EC 3.2.1.35) derived from ovine testes was purchased from Boehringer/Mannheim Corp. (Product #106500, Lot #: 10372425-19 and 10691020-20). One unit of enzyme activity is defined as that amount of enzyme which liberates 1 micromole of N-acetyl-glucosamine per minute at 37° C. and pH 4. Two milliunits (mU) of hyaluronidase (15 NF units) will release 1 micromole of terminal N-acetyl-glucosamine residues in one minute at 37° C. and pH 4.0. National Formulary units are based upon the reduction of turbidity of a solution of a hyaluronic acid/albumin mixture measured spectrophotometrically at 600 nm. Hyaluronidase activity has been shown to be reversibly inhibited by metal ions including $Fe^{2+}$ and $Cu^{2+}$, both of which are strong inhibitors at 0.5 mM, and $CN^-$.

Current methods used for the analysis of hyaluronidase activity involve the spectrophotometric determination of reducing sugars formed upon enzymatic hydrolysis. Hyaluronidase catalyzes the degradation of hyaluronic acid with the liberation of acetylglucosamine residues which can be measured in a colorimetric assay. In the assay, N-acetyl-glucosamine (NAGA) in an alkaline solution is converted to an anhydro sugar. The anhydro sugar is then reacted with 4-dimethylaminobenzaldehyde at an acid pH to form a colored furan derivative. The amount of acetylglucosamine liberated per unit time is a measure of hyaluronidase activity.

The substrate hyaluronic acid is not readily soluble in aqueous buffers. Solutions of hyaluronic acid should be prepared at least 1 day before assay, stored at 4° C., and mixed thoroughly prior to use. The amount of NAGA released is measured by converting the NAGA sugar into its furan derivative, by increasing the acidity of the solution, and reacting this furan derivative with p-dimethylaminobenzaldehyde (DMAB) to form a colored complex which is measured spectrophotometrically at 585 nm.

Hyaluronidase is preferably assayed at 37° C. Hyaluronic acid and NAGA solutions should be prepared fresh weekly. The p-dimethylaminobenzaldehyde solution is stable for a month. Hyaluronidase solutions can be stored for a limited time at 4° C.; however, the enzyme is very stable when stored lyophilized at −20° C. The detection limit of the method for hyaluronidase activity is less than 2 mU (equivalent to 15 NF units) per mg of protein. Variations in the ionic strength of the buffer, the pH, or the amount of sample can alter the final pH of the final color test for acetylglucosamine which functions only in alkaline solution. Hyaluronic acid is not very soluble, is inclined to swell, and must be thoroughly mixed. Chondroitin 6-sulfate can replace hyaluronic acid as substrate but chondroitin 4-sulfate cannot.

Initial Preparation of Reagents for Hyaluronidase Assay

NAGA: A 1 mg/ml solution is prepared by dissolving 10 mg of NAGA in 10 ml of CBSCa 6.7.

Std A: 1 ml NAGA stock is added to 49 ml CBSCa 6.7 (20 μg/ml).

Std B: 500 μl NAGA stock is added to 49.5 ml CBSCa 6.7 (10 μg/ml).

0.8 M $K_2B_4O_7$: 48.88 g $K_2B_4O_7$ is added to 200 ml deionized $H_2O$, heated to solubilize, and the pH is adjusted to 9.1 with 5 N KOH or 6 N HCl.

DMAB: 1 g DMAB is added to 10 ml of acetic acid/hydrochloric acid (8.75 ml acetic acid+1.25 ml HCl). The solution is diluted 1:10 with acetic acid immediately prior to use.

Hyaluronic acid: 62.5 mg of hyaluronic acid is added to 50 ml of CBSCa 6.7. The solution should be prepared 24 hours in advance of assay and stored at 4° C.

Hyaluronidase: 1%, 0.1%, and 0.01% (w/v) solutions are prepared in 0.05 M CBSCa 6.7 with enzyme activities ranging from 1200 to 2100 U/mg.

All solutions are stable for one week when stored at 4° C.

The assay for hyaluronidase activity is performed by adding 200 μl of hyaluronic acid (1.25 mg/ml) and 50 μl of hyaluronidase (1%, 0.1%, 0.01%) to 13×100 test tubes. The mixture is incubated at 37° C. for 10 minutes and cooled under running tap water. To this is added 50 μl of tetraborate (pH 9.1, 0.8 M $K_2B_4O_7$). The solutions are heated for 3 minutes in a boiling water bath, cooled under running tap water, followed by the addition of 1.5 ml of DMAB (1:10), incubated for 20 minutes at 37° C., and again cooled under running tap water. Aliquots are transferred to plastic spectrophotometric cuvettes and the OD at 585 nm is determined immediately (in less than 10 minutes).

| The reagent blank consists of: | The NAGA STD tubes contain: |
| --- | --- |
| 250 μl of CBSCa 6.7 | 250 μl STDS A or B |
| 50 μl $K_2B_4O_7$ | 50 μl $K_2B_4O_7$ |
| 3 min. boil and cool | 3 min. boil and cool |
| 1.5 ml DMAB (1:10) | 1.5 ml DMAB (1:10) |
| 20 min. at 37° C. and cool | 20 min. at 37° C. and cool |
| The sample blank consists of: | The NAGA STD blank consists of: |
| 250 μl Hyaluronic acid | 250 μl NAGA STD A or B |
| 50 μl CBSCa 6.7 | 50 μl CBSCa 6.7 |
| 3 min. boil and cool | 3 min. boil and cool |
| 1.5 ml DMAB (1:10) | 1.5 ml DMAB (1:10) |
| 20 min. at 37° C. and cool | 20 min. at 37° C. and cool |

The degree of color development of complexes of NAGA and DMAB is dependent upon the alkalinity of the borate solution. Below a pH of 9.0 color development for a given amount of NAGA falls off rapidly. High concentrations of normal human serum have been shown to interfere with the development of the colored NAGA/DMAB complexes. The production of color in the test depends upon the formation of an intermediate compound (glucoxazoline) by heating the acetylhexosamine with alkali and the subsequent reaction of this intermediate with DMAB in an acid medium that results in the development of a reddish purple colored complex.

Activity assays were performed for collagenase and hyaluronidase in order to determine the compatibility of the various antibiotics with enzyme activity. Solutions of various antibiotics were prepared at concentrations reflecting peak serum, tissue, and urine levels in clinically encountered dosage regimens and added to 1 and 0.1% solutions of CHT. The antibiotics gentamicin and trimethoprim/sulfamethoxazole (TMP/SMX) showed no inhibition of enzyme activity at all concentrations tested. Nitrofurantoin, tobramycin, and amikacin showed slight inhibition of collagenase activity with nalidixic acid exhibiting the major collagenase inhibition. Amikacin and nalidixic acid strongly inhibited hyaluronidase activity. Additionally, scans of solutions of the antibiotics at 520 and 585 nm (collagenase and hyaluronidase activity assay wavelengths, respectively) revealed little or no interference: TMP/SMX less than 0.03 absorbance units, gentamicin less than 0.01 absorbance units.

C. Endotoxin Removal

Endotoxins are pyrogenic lipopolysaccharide components of gram-negative bacteria. At concentrations of only ng/ml, endotoxins have been shown to exert potent biological effects in man and animals. Maintaining low endotoxin concentrations in biochemical preparations for in vivo purposes is essential.

Administration of parenteral solutions contaminated with endotoxins (pyrogens or fever producers) to patients can result in complications including: lymphocyte migration, complement fixation, release of histamines and altered vascular permeability. These complications may be life threatening depending upon the general health of the patient and the level of endotoxin injected. Endotoxins have been shown capable of binding to membrane receptors, activating lysosomal activity, impairing mitochondrial functions, stimulating prostaglandins, acting as mitogens, inducing macrophage cytotoxicity, stimulating immunological responses, altering hormonal actions, transforming cells, and imitating the effects of lymphokines.

Elimination of endotoxin contamination in aqueous physiological solutions can be difficult. Ultrafiltration techniques are suitable for solutions that contain only small molecules, but not for the removal of pyrogens from solutions of proteins or other macromolecules. Detoxi-Gel® (a registered TM of Pierce Chemical Co., Rockford, Ill.) contains an immobilized ligand (histamine) which has a unique specificity to bind and remove pyrogens from protein solutions and has a capacity for binding endotoxins of 2 mg/ml. Endotoxin contamination is usually measured in terms of endotoxin units (EU). One EU/ml represents an endotoxin concentration of approximately 0.1 ng/ml. Complete removal of all contaminating pyrogens is practically impossible with the best procedures reducing endotoxin contamination to safe levels. Typically safe or pyrogen poor pharmaceutically acceptable preparations of protein solutions contain less than 1.0 EU/ml. Using Detoxi-Gel®, 7500 EU/ml of pure pyrogen has been reduced to less than 1.0 EU/ml in one pass over a 1 ml Detoxi-Gel® column (5 ml of endotoxin solution applied) resulting in an endotoxin removal efficiency of greater than 99%.

Detoxi-Gel® columns are commercially available with the prepacked gel bed protected by two porous disks which protects the columns from drying out if left unattended for brief periods. Additionally, the disks insure that the quantity of solution applied to the column will always be equal to that which comes off the column, thereby facilitating quantitative procedures. The columns are allowed to come to room temperature. The columns are prepared for chromatography by removing the top cap followed by removal of the bottom cap (to prevent air bubbles from entering the gel bed), placed in a vertical holder, and the liquid in the columns drained completely. The columns are then equilibrated in 0.05 M citrate buffered saline (pH 6.7) containing 20 mM $CaCl_2$ with 10 column volumes at a flow rate of 5 to 15 ml/hr. It is recommended that buffer solutions or samples be loaded on the column in known volumes in order to more accurately obtain uniform volumes in the sequential fractions as they pass through the column. Passage of 5 ml of a 1% solution of CHT over a 1 ml Detoxi-Gel® column for endotoxin removal and subjected to 0.22 $\mu$m sterile filtration results in a 10% reduction of enzyme activity.

D. Endotoxin Assay

Preparation of a pyrogen-free injectable solution of collagen/hyaluronidase/Triton® X-100/gentamicin (CHTG) requires testing in an approved Limulus Amebocyte Lysate (LAL) assay system. Bacterial endotoxins are heat stable lipopolysaccharide components of the cell wall of gram-negative bacteria. Endotoxins are capable of producing a wide variety of biological effects including fever, hypotension, and death. The LAL test has been used in the pharmaceutical industry to detect endotoxin contamination in fluids intended for parenteral use. The LAL test is quantitative and can detect endotoxin concentrations too low to produce fever in humans. LAL test results provide a means of identifying deficiencies in pharmaceutical preparations before levels of endotoxins become clinically significant.

Commercially available test kits for endotoxin contamination have been developed by Whittaker M. A. Bioproducts (Walkersville, Md.) and employ the in vitro Limulus Amebocyte Lysate (LAL) test procedure. The LAL test employs a synthetic chromogenic substrate which in the presence of LAL and endotoxin produces a yellow color that is linearly related to the endotoxin concentration. The correlation between the absorbance at 405 nm and the endotoxin concentration is linear in the range of 0.1 to 1 EU/ml. The concentration of endotoxin in an unknown sample is calculated from the absorbance values of solutions containing known amounts of endotoxin standard.

LAL test results may be determined by the colorimetric measurement of proteins precipitated by the lysate. Synthetic peptide substrates linked to a chromophor remain colorless in the absence of endotoxin, while in the presence of endotoxins turns yellow. The assay provides quantitative results sensitive to the ng/ml level and has been standardized against the FDA Bureau of Biologics Endotoxin Reference Standard in Endotoxin Units (EU). Interferences may be caused by trypsin-like enzymes and result in false positive values. Material known to denature proteins or inhibitors of enzyme activity may result in false negative results. All preparations and testing should be done using pyrogen-free water and plasticware.

The chromogenic LAL test is a quantitative, commercially available test for the determination of concentrations of gram-negative bacterial endotoxins. A test sample is mixed with the LAL supplied in the test kit and incubated at 37° C. for 10 minutes. A chromogenic substrate solution is then mixed with the LAL-sample and incubated at 37° C. for an additional 3 minutes. The reaction is stopped with 0.25% acetic acid. If endotoxins are present in the sample, a yellow color appears. The absorbance of the sample is determined spectrophotometrically at 405 nm. The absorbance is directly proportional to the amount of endotoxin present and the concentration of endotoxin present is calculated from a standard curve. Four endotoxin standards spanning the desired concentration range should be assayed along with a blank, all in duplicate. The coefficient of correlation between the mean absorbance of the standards versus their respective endotoxin concentrations should be greater than 0.98. The reproducibility of replicate samples should result in coefficients of variation less than 10% at the 0.4 EU/ml level.

By extending the first incubation to 30 minutes, it is possible to measure concentrations of endotoxin between 0.01 and 0.1 EU/ml. It is important to determine the linearity of the test at this higher sensitivity and to run standards diluted to cover the appropriate lower concentrations of endotoxin to be measured. All materials coming into contact with samples or test material must be pyrogen-free. Glassware may be rendered pyrogen-free by heating at 180° C. for four hours. Aseptic technique must be used. Strict adherence to the time and temperature of incubations throughout the test procedure is essential.

E. In Vivo Procedures

The purpose of treating BPH is to alleviate urinary outflow obstruction. The reduction in size of the obstructive prostatic tissue and the subsequent alleviation of symptoms of urinary obstruction are indicative of successful therapy. Fundamental to the role played by the composition and method of the present invention, is the methodology involved in the evaluation of the therapy. Objective assessment of the effects of the therapy may be measured by standard methods including urodynamic flow analysis, transurethral examination, or transrectal ultrasonography in conjunction with an obstructive symptom scoring chart.

To assess the role of the present invention in relieving obstructive symptoms of BPH, accurate means of quantitating prostatic size and determining peak urinary outflow are essential. Evaluation of the response to treatment of BPH should be based upon objective criteria. Current prostatic imaging techniques and methods of urodynamic analysis have proven effective in the evaluation of therapeutic treatments for BPH.

In view of the variability of the clinical course of BPH in general and within the individual patient in particular, the need exists for extended baseline evaluations before and after therapy. Initial patient evaluation should include: history; physical; symptom scoring; cystoscopy; complete blood count and biochemical profile; measurement of residual urine; and urinary flow rate. Prostate size may be determined with three dimensional transrectal ultrasonography. Following a course of injections, follow-up evaluation must be performed. Post-therapy follow-up of patients treated for prostatic hypertrophy includes: physical examination; cystoscopy; laboratory studies; and imaging procedures. Patients considered to benefit from therapy are those who have clinical improvement with respect to both peak urinary flow rates and symptom scores.

A convention for estimating prostate size on physical examination involves a grading scale ranging from normal through 4+. A normal gland is approximately the size of a horse chestnut, weighs approximately 10 gm and presents as a minimally perceptible impression on rectal examination. A 1+ enlarged prostate is about the size of a plum, weighs about 25 gm and occupies a bit less than one fourth of the rectal lumen. A 3+ enlarged prostate attains the size of an orange, achieves a weight of approximately 75 gm and fills approximately three fourths of a rectal diameter. A 4+ gland may attain the size of a small grapefruit, weigh in excess of 100 gm and fill so much of the rectal lumen that adequate examination is difficult.

Recent advances in ultrasonic imaging instrumentation and techniques have proven useful in the diagnosis, staging, and treatment of diseases involving the prostate and bladder. Three dimensional imaging techniques employing transrectal or transurethral ultrasonic scanning equipment have been shown to be accurate and valuable in assessing the local response of the prostate to treatment. Sonographic voiding studies provide more clinically useful information than the conventional studies that are currently employed. Additionally, the use of transrectal ultrasonography improves the accuracy of prostatic injections by allowing placement of the needle, under ultrasonic guidance, directly into suspicious areas. Transrectal ultrasonography of the prostate allows the anterior portions of the prostate, which cannot be digitally palpated, to be visualized. Intraprostatic anatomy, integrity of the capsule, and seminal vesicles can be also imaged. Furthermore, ultrasonic imaging of the prostate is clinically useful in patients with palpable nodules and offers a method to objectively monitor response to therapy and to identify local recurrence of hyperplastic tissue.

Under ultrasonographic imaging, BPH appears as a diffuse enlargement with the prostatic capsule well defined but thicker than that found in the normal gland. The hyperplastic portion of the gland is composed of multiple fine homogeneous echoes believed to represent small adenomas located in fibrous tissue between the glandular components. Prostatic stromal collagen is the primary factor that determines the echogenicity of the gland. Enzymatic solubilization of the prostatic stromal collagen produces focal areas of necrosis in and around the injection site resulting in a hypoechoic ultrasonic image. Regression in prostatic size may be seen between pre-injection and post-injection scannings. Variable echoes post-injection may be due to: tissue undergoing various degree of solubilization; expansion of previously compressed spongy glandular tissue; blood clots; and granulation tissue.

Prostatic calcifications on ultrasound examination appear as focally dense, highly echogenic areas that produce sonic shadows. In chronic prostatitis, the ultrasonic pattern shows irregularly distributed heterogeneous densities that often extend laterally from the urethra and may distort or obscure the prostatic capsule. Ultrasonically, the malignant prostate appears asymmetrically enlarged and demonstrates areas of increased, decreased, or mixed echogenicity. The presence of early localized carcinoma is demonstrated by localized dense areas without capsular distortion and may be easily confused with prostatic calculi.

The use of transrectal ultrasonography in the determination of prostatic volume has been proven to be a reliable method and has been shown to be accurate to within 5% of the actual prostatic weight. The specific gravity of the prostate is close to 1.0 and the prostatic volume in cubic centimeters is considered equal to its weight in grams. Prostatic weight may be calculated using the simple formula: Weight=0.5 (D1×D2×D3) with D1, D2, and D3 representing diameters of the three dimensions of the prostate. Day-to-day reproducibility of this technique is believed to be about 95%.

Other imaging procedures that may be employed include urinary tract pyelograms, computed tomography, and magnetic resonance imaging techniques. Intravenous pyelograms are of limited value in assessing prostatic size. Computed tomography can reveal the periprostatic area and reveal lymph node size. Intraprostatic detail, however is poor with masses rarely visualized. The detection of enlarged nodes is highly sensitive; however, normal sized nodes may contain microscopic carcinoma. Magnetic resonance imaging, like transrectal ultrasound, reveals intraprostatic anatomy. The technique is as accurate and sensitive as transrectal ultrasound or computed tomography in demonstrating pelvic adenopathy, periprostatic invasion, and seminal vesical involvement.

In vivo mammalian model systems developed to evaluate enzyme therapy should provide data regarding effective dosages as well as information about potential toxic or immunologic side effects. Of the experimental animals, the canine has been considered the most appropriate model for the study of human BPH. The large size of the canine prostate as well as the spontaneous occurrence of BPH in older dogs provide analogies with the human system. In spite of morphological and biochemical differences, the canine prostate offers a suitable experimental model for evaluating the effects of enzyme injection therapy. The ethical and technical restrictions of human experimentation make the development of animal model systems essential in bridging the gap between in vitro studies in the laboratory and the human clinical trial.

Due to limitations in extrapolating data obtained from animal experiments to human conditions, the ultimate evaluation of any biological therapeutic agent should be performed on humans. The results of relieving urinary obstruction secondary to BPH by surgical methods currently in use are good. Nonsurgical methods, to be acceptable, must provide equally effective results and be free from untoward side effects. Properly constructed clinical trials are essential and difficult to perform in an elderly population due to limitations in monitoring the course of the disease and its response to therapy over long periods of time. Clinical studies evaluating therapy must include placebo controlled double blind measurements continuing for at least three years post treatment. The effects of the treatment may vary with the proportion of stromal and epithelial components or upon the dose and duration of the treatment.

In order to more objectively select candidates for treatment with the nonsurgical method of injection and to more accurately monitor the effects of the disclosed composition, the necessary criteria for men with BPH to qualify as candidates for enzyme injection therapy should include moderate to severe symptoms with peak urinary flow rates less than 15 ml/second. Patients to be excluded are those with prior prostatectomy, acute urinary retention, infection, neurogenic bladder, urethral stricture, carcinoma of the prostate, or other life threatening illness.

Clinical studies involving human subjects may involve one or more of the following parameters in order to establish the optimal mode of therapy for the treatment of BPH. The prospective patient population exhibiting quantitative obstructive symptoms due to BPH is screened and suitable candidates for enzyme therapy are selected. Selected patients are skin-tested for allergic reactions by the intradermal injection of 0.1 cc of a pharmaceutically acceptable solution of enzymes. Intralesional prostatic injections with various concentrations of enzymes are performed and may be repeated at weekly or monthly intervals until the desired reduction in prostatic tissue is achieved. Suitable and effective amounts of the enzyme solution can be determined from studies which vary in terms of: concentration or activity of enzymes used, volume of injection, location and nature of tissue to be solubilized, and number of injections required for the relief of obstructive symptoms. Experimental therapy should be terminated when the desired reduction of prostatic tissue is achieved or when no further improvement in symptoms between treatments is observed. Suitable amounts (1–20 cc at concentrations ranging between 0.1%–10%) of a pharmaceutically acceptable solution of enzymes may be injected per treatment. Factors which tend to limit the continuation of collagenolysis include subcapsular containment and loss of enzymatic activity after 24 hours. It should be noted that the effective and optimal solution of enzymes may vary with the type of prostatic lesion to be solubilized. The total number of treatments may vary from 1–10 depending upon the degree of prostatic obstruction. The sequence of tissue repair is thought to involve hemorrhagic infarction, inflammation, formation of acute and chronic fibrous granulation tissue, followed by extracellular matrix formation and remodeling.

F. In Vitro Procedures

In vitro experiments were performed with a number of hydrolytic and proteolytic enzymes that are active at physiological pH in order to determine which enzymes were most effective in solubilizing prostatic tissue. Enzymes initially evaluated included: collagenase, hyaluronidase, elastase, pronase, DNase I, trypsin, chymotrypsin, papain, chymopapain, subtilisin, and dispase. These initial studies involved the in vitro enzymatic solubilization of prostatic tissue chips obtained from the guinea pig, canine, and human.

Further in vitro studies included the injection and subsequent enzymatic solubilization of prostatic tissue in commercially available, surgically excised, whole organ specimens of guinea pig and canine prostates. Specimens of human prostatic tissue from individuals exhibiting BPH (which may be obtained from autopsies, cadaver organ transplant donors, or patients undergoing prostatectomy) were also injected with solutions of hydrolytic enzymes. The degree of prostatic tissue solubilization obtained with the various enzymes was evaluated by means of standard brightfield, epifluorescent, and phase-contrast microscopy. In vitro assays, employing synthetic chromogenic substrates, were developed in order to compare and evaluate the effects of various buffers, surfactants, antibiotics, activators, and inhibitors on enzyme activity.

Procedures for the preparation of 8 $\mu$m frozen tissue sections stained with hematoxylin and eosin were developed in order to compare and evaluate the microscopic histologic changes in prostatic tissue caused by the intraprostatic injection of various solutions of hydrolytic enzymes. For histological examination, the prostate was serially divided into approximately 0.5 cm cross-sections. It is important that these cross-sections traverse the mid-portion of the prostate and include portions of the prostatic urethra. All sections should include the urethral mucosa and the outer margin of the prostatic capsule. The tissue cross-sections were frozen at −20° C., mounted on a pre-cooled cryostat chuck, and 8 $\mu$m thin frozen sections were prepared in a cryostat at −40° C. The thin sections were thaw-mounted on microscope slides, immediately fixed in 95% ethanol, stained with hematoxylin and eosin, and coverslipped with Permount (Fisher, Pittsburgh, Pa.). Alternatively, the tissue cross-sections may be immediately fixed in 4–10% formalin pH 7.2, embedded in paraffin, serially thin sectioned, mounted, and stained with hematoxylin and eosin. Thin tissue sections are obtained every 100 $\mu$m with a total of at least 20 thin sections microscopically examined for each prostate.

Prostatic tissue was cross-sectioned with a scalpel and frozen for thin sectioning in a cryostat. The tissue cross-sections may be frozen at −20° C. or snap frozen at −80° C.

by immersion in dry-ice/acetone solutions. If thin sectioning is to be delayed, the tissue may be stored in a sealed container for several days at −20° C. Prior to thin sectioning, the frozen tissue cross-sections were brought to cutting temperature (−30 to −40° C.) by placing them in the cryostat for at least one hour. Microscope slides were cleaned by dipping in 70% to 95% ethanol. Thin frozen sections suitable for H & E staining (6 to 8 μm thick) were prepared in a cryostat. The cutting temperature, knife blade angle and sharpness, and ambient humidity all influence the quality of thin sections. If the temperature is too low, the tissue tends to fracture and shred. If the temperature is too high, the sections tend to curl up and stick to the knife blade. Low humidity seems to prevent curling of the sections on the knife blade resulting in less distortion of tissue morphology. As the tissue sections come off the knife blade, they can be helped onto the microscope slide with a small camel hair artist's brush. Storing the clean slides at room temperature also aids in picking the tissue sections off of the knife blade and in melting the section to the slide. The prepared slides were immediately fixed in 95% ethanol at 22° C. and subjected to the protocol for H & E staining of frozen sections.

The Hematoxylin and Eosin (H & E) staining procedure for frozen sections was performed as follows using solutions of Harris hematoxylin (James Phillips Co., Minneapolis, Minn.), Lerner Eosin Y (Baxter, McGaw Park, Ill.), 1% lithium carbonate (Sigma), and Americlear (Baxter). Frozen tissue sections (8 μm) were fixed in 95% ethanol for 1 to 30 minutes. The slides were treated to the following steps:

rinsed in deionized $H_2O$ for 30 seconds;
stained in hematoxylin for 1 minute;
washed in warm tap $H_2O$ for 15 seconds;
dipped in dilute $Li_2CO_3$, 2–4 dips (50 μl 1% $Li_2CO_3$ into 50 ml deionized $H_2O$);
washed in deionized $H_2O$ for 15 seconds;
dipped in eosin Y, 10 dips;
dipped in 70% ethanol, 5 dips;
dipped in 95% ethanol, 5 dips;
dipped in 100% ethanol, 10 dips;
again dipped in 100% ethanol, 10 dips;
dipped in Americlear, 10 dips;
again dipped in Americlear, 10 dips; and
immediately coverslipped with Permount In vivo studies were designed to evaluate the safety and effectiveness of the described composition and method of administration for the solubilization of prostatic tissue in the Canine animal model. The degree of dissolution, regression, and involution of prostatic tissue caused by the in vivo intraprostatic injection of the composition was evaluated by in vivo and in vitro ultrasonic scans of the prostate and by the gross and microscopic examination of necropsy tissue. Histopathological evaluation of the effects of the injected composition included examination of the prostate, urethra, bladder, testes, kidneys, liver, heart, and lungs. Additionally, evidence of strictures, fistulas, adhesions, and granulomas was sought in tissues neighboring the injection site.

Following a course of in vivo intraprostatic injections of the composition, according to an approved GLP protocol for in vivo canine studies, the animal was euthanized with an overdose of sodium pentobarbital. The prostate was exposed by a mid-line incision, removed, trimmed of excess debris, and weighed. Upon removal, the prostate was placed in a container with normal saline and then scanned ultrasonically. The ultrasonic images of the prostate were recorded on film. The ultrasonic scans were performed so that the ultrasonic and histological findings could be compared in the same areas as accurately as possible. After the scan, the entire prostate was serially sectioned into 0.5 cm slices, photographed, and prepared for microscopic histopathological examination. Care was taken to preserve the correct anatomical orientation for comparison with the ultrasonograms. When the prostate was scanned in vitro, there was no intervening tissue between the transducer and target tissue and thereby provided an optimal ultrasonic image. The ultrasonic patterns of the in vivo prostate scans were not identical to the pattern obtained in vitro due to the circulation of blood and intervening tissues. However, comparisons were made and good correlations found between the in vivo and in vitro ultrasonic scans.

EXAMPLE 1

Frozen guinea pig prostates were immersed in 0.05 M CBSCa 6.7 containing 20 mM $CaCl_2$ and thawed at 37° C. for 30 minutes. The organs were divided into 500 mg portions and incubated with 1%, 0.1%, and 0.01% concentrations of collagenase in CBSCa 6.7 at 37° C. for various periods of time, ranging from 1 to 3 hours. Guinea pig prostates treated for 2 hours at 37° C. with 1% and 0.1% (24,500 & 2,450 U/ml) solutions of collagenase resulted in the complete dissolution of all tissue components. The 0.01% (245 U/ml) solution resulted in the incomplete dissolution of tissue with remnants of all tissue components remaining intact.

Incubation of guinea pig prostate tissue chips with 1%, 0.1%, and 0.01% solutions (16,000 U/ml, 1,600 U/ml, and 160 U/ml) of hyaluronidase resulted in the solubilization of the glandular acini leaving the vessels and ducts relatively intact. The muscle bundles appeared to be separating and frayed. Guinea pig prostate tissue chips incubated with 1%, 0.1%, and 0.01% solutions of Triton® X-100 resulted in the solubilization of glandular components with separating and frayed muscle bundles. The fluid containing cellular debris consisted of apparently soluble and disorganized clumps of glandular tissue with no evidence of remnants of vessels, ducts, or muscle bundles. The 1% and 0.1% solutions of Triton® X-100 were useful in combination with collagenase and hyaluronidase. Solutions of Triton® X-100 provide a degree of solubilization similar to the effects seen by hyaluronidase and elastase on guinea pig prostate tissue. The relative order of enzyme reactivity towards guinea pig prostate tissue followed: collagenase>pronase>hyaluronidase=Triton® X-100=elastase.

EXAMPLE 2

Canine prostatic tissue chips weighing approximately 500 mg and incubated in 1%, 0.1%, and 0.01% solutions of collagenase were 84%, 60%, and 19% solubilized (by weight), respectively after one hour at 37° C. After 2 hours at 37° C., 97.5%, 80% and 51%, respectively, of the tissue was solubilized. Smooth and striated muscle and the walls of various vessels and ducts appeared to remain relatively intact. The 1% solution resulted in the complete solubilization of all tissue components with a small amount of smooth and striated muscle, blood vessels, and ducts remaining in the 0.1% solution. Tissue chips prepared from canine prostatic tissue and incubated with 0.1% collagenase at 37° C. did not result in the solubilization of bladder tissue, urethra, transitional epithelium, or smooth and striated muscle after 2 hours.

Histologic examination of collagenase treated canine prostatic tissue chips revealed large amounts of stromal and glandular tissue solubilized with the muscle bundles separated and disorganized. Collagen bundles were completely solubilized with vessels and ducts remaining relatively intact. Areas of solubilized tissue were lacking fibroblast nuclei with the glandular epithelium solubilized and fragmented into clumps of cellular and nuclear debris.

Frozen canine prostates were immersed in 0.05 M CBSCa 6.7 and thawed for 30 minutes at 37° C. The organ was cleaned and divided into 500 mg chips. Fresh solutions of hyaluronidase (1%, 0.1%, and 0.01% corresponding to 16,000 U/ml, 1,600 U/ml, and 160 U/ml) were prepared in CBSCa pH 6.7. Canine prostatic tissue chips were weighed and incubated in hyaluronidase solutions with mixing at 37° C. in 0.05 M CBSCa 6.7. The tissue chips were removed and weighed after 1 and 2 hours of incubation at 37° C. The various solutions of hyaluronidase resulted in a relatively low degree of tissue solubilization of all the components of the canine prostate. Canine prostatic tissue exhibited much higher resistance to the solubilizing effects of hyaluronidase than was observed for guinea pig prostate. Muscle bundles appeared frayed with the edges curled. Glandular epithelial cells were solubilized and appeared to be flowing. The blood vessels and ducts remained intact and their surrounding stroma remained organized.

Due to the highly differential selectivity, in terms of substrate activity exhibited by collagenase and hyaluronidase, various combination solutions of these enzymes were investigated for their ability to solubilize canine prostatic tissue. Both collagenase and hyaluronidase were compatible with each other in 0.05 M CBSCa pH 6.7 and marked enhancement of collagenase activity was observed when hyaluronidase was added to solutions of collagenase. Collagenase/hyaluronidase combination solutions increased the degree of solubilization and facilitated diffusion of the solution in canine prostatic tissue. The increased degree of prostatic tissue solubilization resulting from the combination of collagenase and hyaluronidase may be due to an increased accessibility of collagen to collagenase through the depolymerization of ground substance mucopolysaccharides by hyaluronidase. The activity of these two enzymes may be further enhanced by the presence of surfactants and/or by stimulation with low frequency sonic oscillation.

Canine prostatic tissue chips treated with Triton® X-100 solutions appeared relatively insensitive to the surfactant after 4 hours of incubation at 37° C. However, in combination with collagenase, Triton® X-100 effectively enhanced the degree of tissue solubilization as the surfactant aids in exposing basement membrane collagen to the solubilizing effects of collagenase. Additionally, Triton® X-100 aids in the lysis of prostatic cells by solubilizing membrane bound phospholipids.

Among the more specific hydrolases, collagenase and hyaluronidase were more effective in solubilizing canine prostatic tissue than elastase. Of the non-specific proteases, pronase was more effective than dispase. The relative effectiveness of the various enzyme solutions in solubilizing canine prostatic tissue chips was exhibited by the following order of reactivity: collagenase>hyaluronidase=Triton® X-100=elastase>pronase>dispase.

EXAMPLE 3

Frozen canine prostates were immersed in 0.05 M CBSCa 6.7 and thawed at 37° C. for thirty minutes. A fresh solution of 0.1% collagenase (2450 U/ml) was prepared by dissolving 10 mg of collagenase in 10 ml of CBSCa 6.7. The thawed prostate was suspended in 50 ml of CBSCa 6.7 and injected with 1 cc the solution in three different sites via a 22 g needle at a rate of 1 cc/5 min. The injected prostate was incubated for 1 hour at 37° C. The organ was removed from the water bath, examined, and dissected. Gross examination of the injected sites revealed involuted asymmetric areas soft and spongy to palpation, as opposed to noninjected tissue. Upon dissection, the areas of injection appeared as small pockets of focal necrosis approximately 1 cm in diameter filled with a high degree of cellular debris. The organ appeared highly muscular with a relatively low degree of glandular acini and supporting stroma. Gross areas of tissue solubilization were evident. Serial 8 $\mu$m frozen tissue sections were prepared and stained with hematoxylin and eosin for microscopic and histologic examination. Histologic examination of canine prostates injected with collagenase revealed areas of undigested smooth and striated muscle, ducts, and blood vessels.

EXAMPLE 4

Compositions including collagenase, hyaluronidase, and Triton® X-100 were evaluated for their ability to disrupt, degrade and solubilize guinea pig and canine prostatic tissue. The suitability of the enzyme combination in terms of stability and maintenance of activity of each individual component was quantitated by sensitive chromogenic enzyme activity assays.

Frozen canine and guinea pig prostates were immersed in 0.05 M CBSCa 6.7 and the tissues thawed for 30 minutes at 37° C. A 1% solution of collagenase/hyaluronidase/Triton® X-100 (CHT) was prepared by dissolving 26 mg collagenase (24,500 U/mg), 20 mg hyaluronidase (1,600 U/mg), and 20 $\mu$l of Triton® X-100 in 2 ml of CBSCa 6.7. The canine prostate was injected with 2 cc by a 22 g needle. The guinea pig prostate was injected with 0.5 cc via a 25 g needle. The injected prostates were incubated in zip-lip bags at 37° C. for 3 hours. Upon removal from incubation, the injected areas of the canine prostate were slightly involuted, very soft, spongy, and contained a large amount of necrotic fluid. Gross examination of the injected guinea pig prostate following incubations revealed no recognizable external morphology with anatomic landmarks totally obliterated.

The tissues were then sealed in zip-lip polypropylene bags and immersed in a solution of dry-ice/acetone (–80° C.) for four minutes and stored at –20° C. The frozen, enzyme treated tissues were diced with a microtome blade and 8 $\mu$m frozen serial sections were prepared in a cryostat at –40° C. The frozen 8 $\mu$m tissue sections were melted to a warm microscope slide, fixed in 95% ethanol, and subjected to the hematoxylin and eosin staining protocol. Stained sections were also prepared from normal canine and guinea pig prostatic tissue.

Canine prostates injected with 1 cc of a 1% solution of CHT resulted in the solubilization of stromal collagen and glandular acini, with the smooth and striated muscle bundles separated or frayed and disorganized. Fibroblast nuclei were missing. The vessels and ducts remained relatively intact. Guinea pig prostates injected with 1% solutions of CHT resulted in the involution and rather complete solubilization of collagen bundles and glandular acini. Smooth and striated muscle bundles appeared separated and frayed. The ductal endothelium appeared to have been solubilized. Enzyme treated areas revealed solubilizing collagen and smooth muscle bundles which were highly disorganized and lacking nuclei. The nuclei of the glandular acinar epithelium were highly fragmented or missing, resulting in a large amount of necrotic fluid and cellular debris.

EXAMPLE 5

Chips of hypertrophied human prostatic tissue were obtained from biopsy positive patients undergoing surgery by TUR. The chips were placed in a sealed specimen cup and stored at 4° C. for transport to the lab. The tissues studied were either used immediately or stored for further use at −20° C. Frozen tissue was thawed at 37° C. while immersed in 0.05 M citrate buffered saline containing 20 mM $Ca^{2+}$ (pH 6.7).

Tissue samples of BPH obtained during prostatectomy were cut into large cubic fragments (200 to 500 mg) and incubated at 37° C. with a variety of collagenase preparations. The fragments were gently mixed over a 1 to 5 hour time period. The fragments. were removed at hourly intervals, weighed, and returned to the enzyme solution. The effects of 0.1% and 1% solutions of CHT on human prostatic tissue were evaluated and found to be highly effective in disruption, degradation, and dissolution of the stromal and epithelial components. The chips were completely disrupted with the stromal and glandular cells being dispersed as a suspension of single cells. Upon digestion, dispersed epithelial cells could still be recognized as rod shaped cells with a round nucleus at one end of the cell with many cytoplasmic granules, as observed under the phase contrast microscope.

Human prostatic tissue chips obtained by TUR were placed in an air-tight specimen cup, stored and transported to the lab at 4° C. and frozen at −20° C. The prostatic tissue was obtained from a 70 year old male (CAM) with a biopsy diagnosis of BPH and adenocarcinoma. The specimen upon gross examination appeared to be of three different tissue types: glandular, fibromuscular, and nodular. The frozen prostatic chips of the various types (glandular, fibromuscular, and nodular) were immersed in 0.05 M CBSCa 6.7 and thawed for 30 minutes at 37° C. Fresh solutions of 1% and 0.1% CHT were prepared in 0.05 M CBSCa 6.7 by dissolving 38 mg of collagenase, 30 mg of hyaluronidase and 30 µl of Triton® X-100 in 3 ml of the buffer. The solution resulted in a preparation containing 24,500 U/ml collagenase, 16,000 U/ml hyaluronidase, and 1% Triton® X-100. The 0.1% solution of CHT was prepared by a 1:10 dilution of the stock 1% solution (300 µl 1% CHT into 2.7 ml CBSCa 6.7). The 0.1% solution of CHT contained 2,450 U/ml collagenase, 1,600 U/ml hyaluronidase, and 0.1% Triton® X-100. The tissue chips were weighed and incubated in 1% and 0.1% solutions of CHT (500 µl/chip) with mixing at 37° C. The enzyme treated tissue chips were removed and weighed after 1 and 2 hours of incubation.

A differential solubility of the prostatic chips based on tissue type was observed in chips treated with solutions of CHT. The glandular tissue and accompanying collagenous stroma were completely soluble after 2 hours. The fibromuscular tissue was incompletely soluble after two hours; however, the tissue was rather soft, spongy and amorphous indicating definite tissue dissociation, though incomplete. The fibromuscular bundles, however, tended to remain relatively intact. Microscopic examination of the fluid from 1 and 2 hour digests, air dried on slides and stained with hematoxylin and eosin, revealed completely solubilized glandular tissue, free floating clumps of solubilized glandular acini, remnants of various vessels and ducts, and other cellular debris. Slides prepared from the 2 hour digests resulted in the complete solubilization of all glandular components with small remnants of vessels and ducts visible. Elastic fibers were present. Solutions of 1% CHT resulted in more complete cellular and stromal destruction while 0.1% solutions of CHT resulted in incomplete solubilization of the various tissue components with blood clots and calculi remaining insoluble.

Light microscopy of the epithelial clumps obtained after treatment of BPH tissue with collagenase revealed highly fragmented acinar glands. Stromal components were not found in the epithelial clumps of cellular debris. Examination of stroma revealed compact fibromuscular bundles with clear open spaces in the matrix previously occupied by the epithelial glands. There were few, if any, epithelial cells remaining, with considerable damage to fibroblasts and smooth muscle cells evident. However, a few intact, nucleated fibroblasts were observed. Fibromuscular tissue that remained undissolved after 2 hours in 1% CHT at 37° C. contained a large number of elastic fibers. The muscular bundles were frayed, tangled, and beginning to solubilize. The muscle tissue was disorganized and remnants of vessels and ducts were observed.

Solutions of collagenase/hyaluronidase/Triton® X-100, ranging in concentration from 0.1% to 1%, were highly effective in solubilizing hypertrophied human prostatic tissue chips obtained by TUR. The nodular fibromuscular areas exhibited more resistance to dissolution than the glandular or epithelial tissue upon exposure to solutions of CHT. However, over time, all components of stromal and epithelial tissue were soluble. Injected nodules became soft and involuted. Permanent H & E stained 8 µm tissue sections were prepared and demonstrated the effects of tissue disruption, degradation and dissolution by 0.1% and 1% solutions of CHT on human prostatic tissue chips exhibiting adenocarcinoma and BPH.

EXAMPLE 6

Human prostatic tissue chips were obtained by TUR, divided into 500 mg portions, and soaked in citrate buffered saline for 30 minutes. Nodular areas of gross hyperplasia were injected with 0.1 to 1 cc of 0.1% and 1% solutions of the enzymes collagenase and hyaluronidase containing Triton® X-100 and gentamicin (CHTG), all in citrate buffered saline containing calcium at pH 6.7. The injected tissue was incubated in a glass dish at 37° C. for periods of time ranging from 1 to 5 hours. Tissue samples, along with samples of prostatic cell suspensions resulting from the enzymatic digestion, were frozen, cryostat sectioned at 8 µm increments, fixed in 95% ethanol and stained with hematoxylin and eosin.

Human prostatic tissue chips containing fibromuscular nodules were injected with 0.3 cc of 1% and 0.1% solutions of CHTG via a 25 g needle and incubated for three hours at 37° C. The first 0.1 cc which was injected resulted in the swelling of the nodule, with the remaining 0.2 cc tending to leak from the cut surfaces of the nodule. The treated chips were frozen at −20° C. and stored for sectioning and histologic staining with hematoxylin and eosin. After three hours at 37° C., the injected fibromuscular nodules appeared upon gross examination to be soft, amorphous, and involuted around the site of injection. These studies revealed that 1% solutions of CHTG were more effective in solubilizing human prostatic tissue than 0.1% solutions. The adenomatous (glandular) tissue was more susceptible to the solubilizing effects of the proteolytic mixture than pure fibromuscular tissue.

Histological examination of the injected nodules revealed pockets of focal necrosis approximately 1 cm in diameter. Specific areas of focal necrosis immediately surrounding the site of injection were difficult to distinguish from the general diffuse areas of tissue solubilization and disorganization. The areas of complete solubilization formed a gradual transition line with areas of less complete tissue dissociation.

Definite collagenolysis occurred in the injected nodules within a 0.5 to 1.5 cm radius of the injection site. Collagenous fiber bundles disappeared in treated tissue with the dissolved collagen staining faintly and appearing vacuous. Elastic fibers were preserved in areas where the collagen had been completely dissolved. 1% solutions of CHTG were highly effective in the complete solubilization of glandular, collagenous stroma, and the ground substance of human prostatic tissue. The solution was less effective on the smooth muscle components; however, evidence of muscle disorganization and bundle solubilization was observed.

The injected prostatic nodules underwent considerable reduction in overall size and weight. Microscopically, the treated nodules revealed widespread fraying and dispersal of collagen bundles compared to the dense compact collagen seen in the untreated tissue. The mixture of collagenase and hyaluronidase caused extensive dissolution in vitro of the epithelial and stromal components of prostatic tissue. The extent and amount of enzyme induced tissue solubilization was related to the dosage used. The human prostate is spongy, rather porous, and composed of many glands and ducts that tend to promote elimination of injected solutions of enzymes fairly rapidly through the urethra. The degree of solubilization of prostatic tissue is limited by the size of the dose that can be administered. Increased diffusion and spreading of the mixture from the site of initial enzyme deposition is accomplished with increasing dosages of hyaluronidase. The increased diffusion is related to the digestion of the mucopolysaccharide ground substance which embeds the collagen in the connective tissue but is not subject to the action of collagenase.

Human prostatic tissue chips obtained by TUR and containing hyperplastic nodules of benign hypertrophy and malignant adenomatous tissue were injected with various concentrations of hydrolytic enzymes. Effective concentrations of hyaluronidase and collagenase resulted in a grossly visible zone of solubilization of prostatic tissue centering around the injection site. The diameter of solubilization or necrosis was not greater than that of the bleb raised at the time of injection. Smaller doses of the enzymes resulted in microscopic evidence of solubilization with the areas of microfocal necrosis remaining approximately the size of the initial injection bleb.

The enzymes collagenase and hyaluronidase have been shown useful in the dissolution of prostatic tissue when administered in an effective amount by in vitro intraprostatic injection. Areas of solubilization were confined to the subcapsular tissue within the injected lobe and its immediate vicinity. Scattered areas of necrosis appeared throughout the glandular tissue. The percent of tissue solubilized was apparently directly related to dosage, as increases in the radius of lysis were accomplished with increasing dosages of hyaluronidase.

EXAMPLE 7

To evaluate the safety and effectiveness of the composition of the present invention, in vivo injections of the composition were carried out in the Canine animal model according to an approved GLP protocol. The degree of necrosis of prostatic tissue was evaluated by in vivo and in vitro ultrasonic scans and by the gross and microscopic examination of necropsy tissue. Histopathological examination of the effects of the test composition included examination of the prostrate, urethra, bladder, testes, kidneys, liver, heart, and lungs. Additionally, evidence of strictures, fistulas, adhesions, and granulomas were sought in tissues neighboring the injection site.

Records maintained included: animal history and physical data (approximate age, weight, breed); dates procedures were performed; charts of clinical progress and adverse reactions; laboratory test results; medications administered (date, dose, and route); ultrasound scan images; prostatic weights; necropsy and histopathology reports and slides. Charts recording the clinical progress of the animal were maintained especially noting the presence, degree, and duration of hematuria, hemospermia, urinary tract infection, urinary retention, and medications administered throughout the course of the protocol. Evidence of urinary retention was determined by monitoring fluid intake and output, and by analysis of BUN, creatinine, and electrolyte concentrations.

In order to prepare a solution of the disclosed composition suitable for parenteral administration, 100 ml of 0.05 M Citrate Buffered Saline containing 20 mM $CaCl_2$ (pH 6.7, CBSCA) was prepared with freshly distilled, deionized, sterile, pyrogen-free water (Gibco, Grand Island, N.Y.). One ml of Triton® X-100 and 1.5 ml of a 10 mg/ml sterile solution of gentamicin sulfate (Sigma) were added so as to obtain a final concentration of 1% (v/v) for Triton® X-100 and 150 µg/ml for gentamicin (CBSCA-TG).

Lyophilized preparations of Collagenase (Type XI-S, Sigma) and hyaluronidase (106-500, Boehringer/Mannheim) were reconstituted in CBSCA-TG in order to achieve final enzyme concentrations of approximately 0.1% (2,450 U/ml collagenase and 1,600 U/ml hyaluronidase). Collagenase (50 mg, Lot # 17F-6814, 1,970 U/mg) and hyaluronidase (40 mg, Lot # 10372425-19, 1,600 U/mg) were added to 4 ml of CBSCA-TG yielding approximately a 1% stock solution (CHTG) of collagenase (24,500 U/ml) and hyaluronidase (16,000 U/ml). A 0.1% working solution of CHTG was prepared by diluting the 1% CHTG stock solution 1:10. An aliquot of 1% CHTG (700 µl) was diluted and mixed in 6.3 ml of CBSCA-TG. The resulting 0.1% CHTG solution contained final concentrations of approximately 2,450 U/ml collagenase, 1,600 U/ml hyaluronidase, 1% Triton® X-100 (v/v) and 150 µg/ml gentamicin sulfate.

For endotoxin removal, a 1 ml Detoxi-Gel® (Pierce) column was equilibrated at room temperature with CBSCA-TG by passing 10 column volumes of the buffer through the column at a flow rate of approximately 10 ml/hr. Seven ml of the 0.1% CHTG solution was applied to the column and eluted under aseptic conditions, into a sterile, pyrogen-free, plastic test tube at a flow rate of approximately 6 to 8 ml/hr. Six ml of the pyrogen-free eluate (0.1% CHTG) was collected and sterile filtered by passing the solution through a certified, sterile, pyrogen-free, 0.2 µm, polysulfone, disposable, syringe filter into a sterile, pyrogen-free, plastic test tube. A 1 ml aliquot of the sterile filtered, pyrogen-free, 0.1% solution of CHTG was aseptically removed for endotoxin and enzyme activity testing. Preparations of 0.1% CHTG exhibiting less than 1.0 EU/ml (LAL chromogenic pyrogen test, Whittaker) and enzyme activities for collagenase with an OD greater than 1.0 at 520 nm (Azocoll® assay) and for hyaluronidase with an OD greater than 0.2 at 585 nm (NAGA assay) were routinely approved for in vivo parenteral injections.

A random source, 33 kg, adult, male Canine arrived conditioned, and heart-worm negative. The experimental animal was confirmed normal by physical examination, complete blood count, serum chemistries, urinalysis, and quantitative urine culture. The animal was not fed for 24 hours prior to the experimental injection of the test composition. Two hours prior to the intraprostatic injection of the composition, the animal was given a prophylactic, intramuscular injection of gentamicin (1 to 3 mg/kg) and a tepid water enema.

The experimental Canine (8HC55) was pre-anesthetized with a combination of atropine sulfate (0.04 mg/kg) and acetylpromazine maleate (0.1 mg/kg) administered intramuscularly. Anesthesia was induced with 4.8 ml of oxymorphine (1.5 mg/ml) given intravenously. Just prior to injection of the test composition, a baseline transabdominal ultrasound scan of the prostate was obtained and recorded on film. The prostatic urethra was catheterized with a 5–7 french, end-hole, balloon catheter (Swan Ganz Catheter, Edwards Laboratories, Santa Ana, Calif.). The balloon tip of the catheter was centrally positioned within the prostatic urethra under ultrasonic guidance and inflated with saline in order to prevent the immediate egress of the injected test composition through the urethra.

Transrectal intraprostatic injection of the test composition was performed under ultrasonic guidance with a slightly curved 22 g×20 cm flexible aspiration biopsy needle in conjunction with a Franzen needle guide (Precision Dynamics, San Fernando, Calif.). A gloved index finger and needle guide were inserted into the rectum. The prostate was digitally palpated while the needle was inserted through the guide and advanced into the prostate. Approximately 2.5 ml of the composition (0.1% CHTG) was injected into the right lobe of the prostate, with the left lobe serving as a control.

Upon injection, vital signs were monitored for symptoms of toxic, allergic, or other adverse reactions. The Swan Ganz catheter was removed 2 hours post-injection with a small amount of blood stained fluid observed. The animal progressed well and exhibited no signs or symptoms of any adverse reactions. The clinical progress of the animal was uncomplicated and uneventful throughout the course of the eight day protocol. On the day following injection, a transabdominal ultrasound scan of the prostate was obtained as were blood and urine specimens. On the final day of the protocol, an additional in vivo transabdominal ultrasound scan was obtained along with further blood and urine specimens for testing, analysis, and culture.

Eight days post-injection, the animal was euthanized with an intravenous overdose of sodium pentobarbital and immediately necropsied. The prostate was exposed by a mid-line incision, removed, trimmed of excess debris, and weighed. The excised prostate was placed in a container of saline and scanned in vitro ultrasonically. After the scan, the entire prostate was sliced into approximately 0.5 cm transverse sections, photographed, and prepared for microscopic histopathological examination. The transverse sections of the prostate included the urethral mucosa and the outer margin of the prostate. The tissue sections were immediately fixed in 10% neutral phosphate buffered formalin, embedded in paraffin, thin sectioned at 6 µm, mounted on microscope slides, and stained with hematoxylin and eosin. The fixed and stained tissue sections were then examined under brightfield light microscopy for infarcts, hemorrhage, necrosis, dissolution of collagen, and alteration of morphology. Care was taken to preserve the correct anatomical orientation for comparison with the ultrasonogram.

At necropsy, the experimental Canine (8HC55) exhibited a final body weight of 27 kg. Representative samples of the bladder, urethra, testes, kidneys, liver, heart, and lungs were removed and fixed in 10% neutral buffered formalin. The tissues were embedded in paraffin, thin-sectioned at 6 µm, stained with hematoxylin and eosin, and examined microscopically. Evidence of damage to vital organs (heart, lungs, liver, kidneys), neighboring tissues (bladder, urethra, testes), denudation of prostatic urethral epithelium, strictures, fistulas, adhesions, and granulomas at or near the injection site was sought.

The gross pathology of the abdominal cavity revealed an elliptical hemorrhagic lesion confined to the right lobe of the prostate. The ventral surface of the right prostatic lobe was dark red and thickened from about the middle to the caudal end of the prostate. The prostate gland measured 3.0×3.4× 2.2 cm and weighted 17.4 grams. The organ/body weight ratio was 0.65 g/kg. The pelvic urethra, bladder, testes, kidneys, ureters, liver, heart, and lungs appeared grossly normal. There was no evidence of injection/enzyme induced lesions in the pelvic lymph nodes. Periurethral hemorrhage was visible.

Transverse sections of the prostate revealed a 1 cm diameter area of dark red hemorrhage in the lower right quadrant of the gland form the middle to the caudal end of the right lobe. The hemorrhagic lesion appeared to result from the experimental injection of the test composition. Microscopically, the area of necrosis at the site of the enzyme injection was primarily localized to the middle transverse section of the prostate and involved several adjacent lobules in the ventro-medial area of the right lobe. There was a breakdown of lobular architecture with necrosis of alveolar walls and large deposits of fibrin and erythrocytes. Inflammatory cells were conspicuously absent in the necrotic area. Prostatic stroma adjacent to the area of acute necrosis revealed focal hemorrhages, disruption and fragmentation of collagen, degeneration and necrosis of smooth muscle, and proliferation of fibroblasts.

Prostatic lobules bordering the injection site had both epithelial and stromal changes. Alveoli lined by cuboidal epithelial cells often contained flocculent or homogeneous secretory material. The interlobular stroma and trabeculae were pale-stained and separated by erythrocytes and clear spaces. The inner portion of the prostate contiguous with the apex of necrotic prostate lobules had stromal hemorrhages and disrupted periurethral glands. The prostatic urethral epithelium was intact; although, the urethral lumen appeared deviated by the inflammatory process.

Degenerative changes also were noted within bundles of prostatic striated muscle including necrosis, myelosis, cytoplasmic vacuolation, fiber atrophy, and proliferation of sarcolemma cell nuclei. Hemorrhages and fibrinoid arteritis (one vessel) were noted in the stroma between striated muscle bundles. The walls of some capsular arteries were partially replaced by fibrinoid change. Perivenous fibrinoid deposits were also noted. The transverse section taken anterior to the injection site appeared to have an enzymatically digested space with an irregular outline. The transverse section immediately caudal to the injection site had a hemorrhagic focus in the periurethral stroma, but no other parenchymal changes.

Hemorrhage and fibrin deposits were seen in adipose tissue around the urethra where it begins to emerge from the prostate gland. The outer wall of striated urethral muscle showed degenerative changes similar to those previously described. Most of the urethra, except for muscle fibers at the periphery of the tunica muscularis and the periurethral adipose tissue, was normal. There were localized changes in the periurethral fat such as hemorrhage, fibrin deposition, and fibrinoid arteritis (one artery). Adjacent striated muscle fibers were degenerative.

No abnormal histopathological findings consistent with the injection of the experimental enzyme composition were observed in the urinary bladder, testes, seminiferous tubules, kidneys, liver, heart, and lungs. Prostatic changes ascribed to the experimental injection of the enzyme composition were localized primarily in the corpus, in the ventral section of the middle one-third of the right lobe. Destruction of the internal portion of the prostate, but not the prostatic urethra was found. There was no evidence of strictures, fistulas, adhesions, or granulomas at or near the injection site. The microscopic changes observed in the prostate consisted primarily of hemorrhagic necrosis involving the stromal and epithelial cells with a breakdown of lobular architecture, disruption and fragmentation of collagen, and the degeneration and necrosis of smooth muscle.

EXAMPLE 8

So as to further evaluate the safety and effectiveness of the disclosed composition, long-term (60 day) studies were carried out in the Canine animal model according to an approved GLP protocol. The effects of the in vivo, intraprostatic injection of the composition were evaluated by the laboratory analysis of blood and urine specimens, by in vivo and in vitro ultrasonic scans, and by the gross and microscopic examination of necropsy tissue.

Upon arrival, a random source, 28 kg, conditioned, adult male Canine (8IC76) was given a physical examination. The experimental animal was confirmed as normal by laboratory evaluations including complete blood count, serum chemistries, urinalysis, and quantitative urine culture. The injection composition was prepared as previously described and contained 2,400 U/ml collagenase, 1,600 U/ml hyaluronidase, 1% (v/v) Triton® X-100, 150 µg/ml gentamicin, and 20 mM $CaCl_2$ in 0.05 M citrate buffered saline (pH 6.7). Removal of pyrogens and sterile filtration resulted in a preparation (Injection Composition "G") that exhibited an endotoxin level of 0.29 EU/ml by the LAL chromogenic pyrogen test. The laboratory animal was not fed for 24 hours prior to the surgically assisted, direct intraprostatic injection of the disclosed enzyme composition.

On day 1 of the protocol, two hours prior to the intraprostatic injection of the composition, the animal was given a prophylactic, intramuscular injection of gentamicin (1 to 3 mg/kg) and a tepid water enema. A urinary catheter was not placed. The animal was anesthetized, a surgical laparotomy exposing the ventral capsule of the prostate was performed, and approximately 3.5 cc of Injection Composition "G" was injected (via 22 g 1.5" needle) directly into the right lobe of the prostate (leaving a "Z" shaped needle track). The left prostatic lobe served as a control.

Upon injection, vital signs were monitored for symptoms of toxic, allergic, or other adverse reactions. The animal's recovery was normal and no signs or symptoms of any adverse reactions to the injection composition were observed. The clinical progress was uncomplicated as the animal remained clinically normal throughout the course of the 60 day protocol. On the day following injection, a trans-abdominal ultrasound scan of the prostate was obtained as were blood and urine specimens. Urinalysis on day 2 of the protocol revealed hematuria. Laboratory evaluations including complete blood counts, urinalysis, urine cultures, and serum chemistry profiles were all within normal limits on days 7, 15, 29 and 58. Urinalysis on day 58 revealed a few spermatozoa. Additionally, noninvasive, in vivo transabdominal ultrasound scans of the prostate were obtained and recorded on film on days 7, 15, 29, 43, and 58 of the protocol.

Throughout the course of evaluation, the right prostatic lobe became asymmetrically-cavitated (involuted) with the overall dimensions of the prostate appearing to regress. Correspondingly, over time, the dimensions of the enzyme-induced necrotic lesion also regressed. Direct intraprostatic injection of the enzyme composition caused the overall regression in size and asymmetric involution of the right prostatic lobe at and near the site of injection. The enzyme-induced lesion, regression, and involution of the right prostatic lobe appeared sonographically as a cavitation and grossly as an indention or sunken area.

A "blind" review of the in vivo, transabdominal sonograms (hypoechoic regions indicating areas of tissue necrosis, hemorrhage, and edema) obtained throughout the course of the protocol for Canine 8IC76 revealed the following:

On day 7, the prostate measured 3×3 cm and exhibited symmetrical lobes. A prominent hypoechoic region measuring 2.5×1.5 cm was observed in the right lobe ranging from the ventral anterior to mid-dorsal portion of the lobe.

On day 15, the prostate measured 3×3 cm, exhibited symmetrical lobes, and areas of patchy hypoechoic foci measuring 1.5×1.5 cm in the ventral anterior portion of the right lobe.

On day 29, the prostate measured 3×2.5 cm, had symmetrical lobes, and exhibited a coalescent hypoechoic focus measuring 1.5×1.5 cm in the anterior ventral portion of the right lobe.

On day 43, the prostate measured 3×2.5 cm with the right ventral lobe exhibiting a slight cavitation and a more uniform coalescent hypoechoic focus. The size of the hypoechoic lesion measured 1.25×1.25 cm.

On day 58, the prostate measured 3×2.5 cm with the right ventral lobe appearing slightly asymmetric (less round) and cavitated. Hypoechoic regions indicating a necrotic lesion, hemorrhage or edema were not found.

On the final day of the protocol, 58 days post-injection, the animal was euthanized with an intravenous overdose of sodium pentobarbital and immediately necropsied. The prostate explant was placed in a container of saline and scanned ultrasonically in vitro. The in vitro ultrasonic scan of the injected prostate revealed prostatic dimensions of 3×2.75 cm and a hypoechoic region measuring 1.5×1.25 cm in the ventral and mid-portion of the right prostatic lobe. The right ventral surface of the right lobe appeared slightly cavitated (involuted). Throughout the course of the protocol, the right prostatic lobe appeared to regress slightly in overall size.

After the ultrasonic scan, the entire prostate was sliced into approximately 0.5 cm transverse sections, photographed, and prepared for microscopic histopathological examination. Care was taken to preserve the correct anatomical orientation for comparison with ultrasonograms. The transverse sections of the prostate included the urethral mucosa and the outer margin of the prostate. The tissue sections were fixed in formalin, embedded in paraffin, thin sectioned, mounted on microscope slides, and stained with hematoxylin and eosin. The fixed and stained prostatic tissue sections were then examined under bright-field microscopy.

At necropsy, experimental Canine 8IC76 had a final body weight of 27 kg. The surgical site in the groin region was nicely healed. Representative samples of the prostate, bladder, urethra, testes, kidneys, liver, heart, and lungs were removed and prepared for histopathological examination. Additionally, evidence of strictures, fistulas, adhesions, and granulomas were sought in tissues neighboring the injection site.

The gross pathology of the abdominal cavity revealed the prostate gland to be small and free of adhesions between the capsule and rectogenital space dorsally. The anterior lateral surface of the right prostatic lobe had an involuted or sunken area (cavitation) about 1.3 cm in diameter. This lesion was about 1 cm distal to the cranial pole of the prostate gland. The prostate gland weighed 18.74 g and measured 3.5×3.2× 2.4 cm. The organ to body weight ratio was 0.70 g/kg. Transverse sections of the prostate revealed a triangular shaped tan area 1.2 cm deep with the apex toward the periurethral prostate. This area appeared in the second 0.5 cm cross-sectional slice of the prostate midway between the dorsal and ventral surfaces of the right lobe. Other slices of the prostate were essentially normal in color and texture. No other abnormalities were noted in the genito-urinary system. No significant lesions that could be ascribed to the experimental injection were noted in the thoracic cavity. The sunken area (cavitation) in the right lobe of the prostate appeared to result from experimental injection of the composition.

The histopathological appearance of the prostate varied from lobule to lobule and from right to left lobes making interpretation of the effects of injection more difficult to pinpoint. At the presumed site of injection, one prostatic lobule had undergone subtotal atrophy. This was characterized by atrophy of prostatic alveoli and ducts with a corresponding increase in intralobular fibromuscular stroma. The prostatic capsule covering the atrophic lobule and several adjacent lobules was thickened and fibrotic. The capsule and atrophic lobule were infiltrated by a modest population of macrophages (many pigment laden), plasma cells and lymphocytes. A few buds of hyperplastic epithelium with or without stromal cores were seen in the lumina of some glands. In proximity to the atrophic prostatic lobule, periurethral prostatic glands and ducts were largely replaced by stroma. A prostatic lobule adjacent to the atrophic lobule also had a locally extensive area of interstitial fibrosis but with less severe glandular atrophy. Thus, it would appear that the injection site in the right prostatic lobe involved several adjacent prostatic lobules. The left prostatic lobe, however, also had lobules with focal areas of interstitial fibrosis, and focal interstitial infiltrates of lymphocytes and plasma cells. The periprostatic urethral tissue was not significantly altered. Prostatic lesions, believed to be ascribed to injection of the enzyme composition, were localized to one or two lobules of prostatic tissue in the right lobe. Alveolar atrophy, interstitial fibrosis and scant chronic inflammatory cells characterized these lesions. Capsular fibrosis was also evident in this area.

The significant histopathological findings in the other tissues examined revealed a single focus of lymphocytes and plasma cells (of minimal degree) present beneath the transitional epithelium of the pelvic urethra. Several veins of the urinary bladder subserosal tissue were cuffed by infiltrates of lymphocytes, plasma cells, and a few eosinophils. No lesions were found in the testes.

The invention has been described with reference to various specific and preferred embodiments and techniques. However, it should be understood that many variations and modifications may be made while remaining within the spirit and scope of the invention.

What is claimed is:

1. A composition for treating prostatic hypertrophy in living mammals, comprising:
    a therapeutically effective concentration of collagenase and a therapeutically effective concentration of hyaluronidase, the composition being suitable for administration by direct intraprostatic injection;
    the concentration of the collagenase and hyaluronidase being effective to cause the dissolution and regression of obstructive, hypertrophied, living prostatic tissue; the concentration of the hyaloronidase being about 1,600 to about 160,000 U/ml.

2. The composition of claim 1, wherein said collagenase is present at a concentration of about 250 to 250,000 U/ml.

3. The composition of claim 2 wherein said collagenase is present at a concentration of about 2,500 to 25,000 U/ml and hyaluronidase at a concentration of about 1,600 to 16,000 U/ml.

4. The composition of claim 1 further including an effective amount of a nonionic surfactant.

5. The composition of claim 4 wherein said surfactant is selected from the group consisting of ethylene oxide esters of $C_{10}$–$C_{20}$ fatty acids, and ethylene oxide esters of $C_8$–$C_{22}$ alkyl alcohols.

6. The composition of claim 5 wherein said nonionic surfactant is either octylphenyl polyoxyethylene oxide or octylphenoxy polyethoxyethanol.

7. The composition of claim 4 wherein said nonionic surfactant is present at a concentration of about 0.1% to 10% by volume.

8. The composition of claim 7 wherein said nonionic surfactant is present at a concentration of about 0.5% to 5% by volume.

9. The composition of claim 1 further including an antibiotic selected from the group consisting of aminoglycosides, sulfonamides, penicillins, cephalosporins, basic macrolides, tetracyclines, polymyxins, fluoroquinolones, lincomycin, clindamycin, chloramphenicol, nitrofurantoin, and nalidixic acid.

10. The composition of claim 9 wherein said antibiotic is gentamicin sulfate.

11. The composition of claim 9 wherein said antibiotic is present at a concentration of about 1.5 to 150 $\mu$g/ml.

12. The composition of claim 11 wherein said composition comprises a sterile pyrogen-free solution of about 2,500 to 25,000 U/ml collagenase, 1,600 to 16,000 U/ml hyaluronidase, 0.5% to 5% by volume of a nonionic surfactant, and 1.5 to 150 $\mu$g/ml of an antibiotic; said composition provided in a buffered, isotonic, aqueous carrier comprising about 0.05 M to 0.1M sodium citrate, about 0.15 M to 0.2 M sodium chloride, about 0.02 M to 0.05 M calcium chloride, having a pH of about 6.7 to 7.0.

13. The composition of claim 11 further including a pharmaceutically acceptable aqueous carrier solution having a physiologic pH.

14. The composition of claim 13 wherein said aqueous carrier comprises 0.02 M to 0.1 M sodium citrate, 0.1 M to 0.2 M sodium chloride, 0.01 M to 0.05 M calcium chloride, and has a pH of about 6.5 to 7.5.

15. The composition of claim 14 wherein said aqueous carrier comprises 0.05 M to 0.1 M sodium citrate, 0.15 M to 0.2 M sodium chloride, 0.02 M to 0.05 M calcium chloride, and has a pH of about 6.7 to 7.0.

16. The composition of claim 13 wherein said aqueous carrier is a sterile, pyrogen-free, buffered, isotonic, aqueous carrier.

17. The composition of claim 16 wherein said aqueous carrier is selected from the group consisting of citrate buffered saline, tris buffered saline, and Ringers saline.

18. The composition of claim 17 wherein said aqueous carrier comprises citrate buffered saline containing calcium ions.

19. The composition of claim 1 wherein the concentration of the hyaluronidase is about 1,600 to 160,000 U/ml.

20. The composition of claim 1 wherein said composition is provided in a pharmaceutically acceptable aqueous carrier solution having a physiologic pH.

21. The composition of claim 11 wherein said antibiotic is present at a concentration of about 10 to 25 µg/ml.

22. The composition of claim 9 wherein said antibiotic comprises trimethoprim/sulfamethoxazle.

23. The composition of claim 22 wherein said antibiotic is present at a concentration of about 1 to 10 µg/ml trimethoprim and 30 to 105 µg/ml sulfamethoxasole.

24. The composition of claim 23 wherein said antibiotic is present at a concentration of about 5 to 10 µg/ml trimethoprim and 50 to 105 µg/ml sulfamethoxazole.

25. The composition of claim 20 wherein said aqueous carrier is a sterile, pyrogen-free, buffered, isotonic, aqueous carrier.

26. The composition of claim 25 wherein said aqueous carrier is selected from the group consisting of citrate buffered saline, tris buffered saline, and Ringers saline.

27. The composition of claim 26 wherein said aqueous carrier comprises citrate buffered saline containing calcium ions.

28. A kit for treating prostatic hypertrophy in living mammals, comprising:

sterile sealed vials containing at least one separate injectable unit-dosage of a composition comprising a therapeutically effective concentration of collagenase, hyaluronidase, and a nonionic surfactant;

the concentration of the collagenase and hyaluronidase being effective to cause the dissolution and regression of obstructive, hypertrophied, living prostatic tissue;

the concentration of the hyaluronidase being about 1,600 to about 160,000 U/ml;

all provided in a pharmaceutically acceptable aqueous carrier suitable for injection into living mammals.

29. The kit of claim 28 wherein said at least one separate injectable unit-dosage comprises collagenase at a concentration of about 250 to 250,000 U/ml.

30. The kit of claim 29 wherein said at least one separate injectable unit-dosage is about 1 to 20 ml.

31. The kit of claim 28 wherein said sterile sealed vials contain a lyophilisate of said composition; whereupon reconstitution with sterile pyrogen-free water provides at least one separate injectable unit-dosage of about 1 to 20 ml of said composition which may be withdrawn as a pharmaceutically acceptable solution for intraprostatic injection into living mammals.

* * * * *

UNITED STATES PATENT AND TRADEMARK OFFICE
CERTIFICATE OF CORRECTION

PATENT NO.     : 6,296,847 B1
DATED          : October 2, 2001
INVENTOR(S)    : Gokcen et al.

It is certified that error appears in the above-identified patent and that said Letters Patent is hereby corrected as shown below:

Column 11,
Line 9, "early." should read -- early --

Column 43,
Line 19, "fragments. were" should read -- fragments were --

Column 52,
Line 11, "hyaloronidase" should read -- hyaluronidase --
Line 42, "claim 11" should read -- claim 4 --

Column 53,
Line 12, "sulfamethoxazle" should read -- sulfamethoxazole --

Signed and Sealed this

Eighteenth Day of February, 2003

JAMES E. ROGAN
*Director of the United States Patent and Trademark Office*